United States Patent
Sotos et al.

(10) Patent No.: US 7,282,027 B2
(45) Date of Patent: Oct. 16, 2007

(54) SERVICE CENTER SYSTEM AND METHOD AS A COMPONENT OF A POPULATION DIAGNOSTIC FOR SLEEP DISORDERS

(75) Inventors: John G. Sotos, Palo Alto, CA (US); John L. Branscum, Jr., Belmont, CA (US)

(73) Assignee: Apneos Corporation, Palo Alto, CA (US)

( * ) Notice: Subject to any disclaimer, the term of this patent is extended or adjusted under 35 U.S.C. 154(b) by 1003 days.

(21) Appl. No.: 10/214,792

(22) Filed: Aug. 7, 2002

(65) Prior Publication Data

US 2004/0030224 A1 Feb. 12, 2004

(51) Int. Cl.
*A61B 5/00* (2006.01)
(52) U.S. Cl. .............................. 600/300; 128/920
(58) Field of Classification Search ................ None
See application file for complete search history.

(56) References Cited

U.S. PATENT DOCUMENTS

| | | | |
|---|---|---|---|
| 4,982,738 A | 1/1991 | Griebel | |
| 5,275,159 A | 1/1994 | Griebel | |
| 5,671,733 A | 9/1997 | Raviv | |
| 5,782,240 A | 7/1998 | Raviv | |
| 5,792,067 A | 8/1998 | Karell | |
| 5,797,852 A | 8/1998 | Karakasoglu | |
| 5,853,005 A | 12/1998 | Scanlon | |
| 5,879,313 A | 3/1999 | Raviv | |
| 5,954,050 A * | 9/1999 | Christopher | 128/204.23 |

(Continued)

OTHER PUBLICATIONS

American Sleep Disorders Association, Clinical Practice Review Committee. Role and qualifications of technologists performing polysomnography. ASDA News. 1998;5(3):26,35.

(Continued)

*Primary Examiner*—Max Hindenburg
*Assistant Examiner*—Michael C Astorino
(74) *Attorney, Agent, or Firm*—Townsend and Townsend and Crew LLP

(57) ABSTRACT

A method for evaluating sleep disorders in mammals and distributing control information related to the sleep disorders through electronic communication networks. The method includes acquiring analog information related to physiological signals through a mobile device from a mammal user. The mammal user is at a geographic location outside of a sleep laboratory staffed by trained technicians. The mobile device is coupled to a sensing device, which is coupled to monitoring region(s) of the mammal. The method includes converting the analog information into a digital format using a signal processing device and transmitting information related to the physiological signals in the digital format to one or more service computers through an electronic communications network. Each of the service computers is operably coupled to a health information service facility. The method determines if the mammal user has related control information at one of the health information service facilities. The related control information is received through the communication network. The method processes the information related to the physiological signals at one or more of the service computers to provide a report associated with the information related to the physiological signals and the mammal user. The method communicates report information in the report associated with the information related to the physiological signals upon indication of receipt of at least control account information of the mammal user based upon the determining the related account information.

40 Claims, 12 Drawing Sheets

U.S. PATENT DOCUMENTS

| | | |
|---|---|---|
| 5,961,447 A | 10/1999 | Raviv |
| 6,045,514 A | 4/2000 | Raviv |
| 6,120,441 A | 9/2000 | Griebel |
| 6,168,568 B1 | 1/2001 | Gavriely |
| 6,171,258 B1 | 1/2001 | Karakasoglu |
| 6,213,955 B1 | 4/2001 | Karakasoglu |
| 6,261,238 B1 | 7/2001 | Gavriely |
| 6,470,885 B1 * | 10/2002 | Blue et al. .............. 128/204.18 |
| 6,532,960 B1 * | 3/2003 | Yurko ................... 128/204.26 |
| 6,796,305 B1 * | 9/2004 | Banner et al. ......... 128/204.21 |

OTHER PUBLICATIONS

E.M. Ball, et al. Diagnosis and treatment of sleep apnea within the community. The Walla Walla Project. *Arch Intern Med.* 1997;157(4):419-24.

G.M. Corbo, et al. Snoring in 9- to 15-year-old children: risk factors and clinical relevance. Pediatrics. 2001;108(5):1149-54.

N.R. Kramer, et al., The role of the primary care physician in recognizing obstructive sleep apnea. Arch Intern Med. 1999;159(9):965-8.

N.C. Netzer, et al. Using the Berlin Questionnaire to identify patients at risk for the sleep apnea syndrome. Ann Intern Med. 1999;131(7):485-91.

T. Young, et al. Estimation of the clinically diagnosed proportion of sleep apnea syndrome in middle-aged men and women. Sleep. 1997;20(9):705-6.

Sleep Solutions Inc. NovaSom QSG Technology Summary. Downloaded 11 pages on Jul. 21, 2002 from: http://www.sleep-solutions.com/phys/phys_novasom_qsg.htm.

SNAP Laboratories LLC. Downloaded 3 pages on Jul. 21, 2002 from: (1) http://www.snaplab.com/home.htm (2) http://www.snaplab.com/mp_demo.htm (3) http://www.snaplab.com/mp_fact.htm.

* cited by examiner

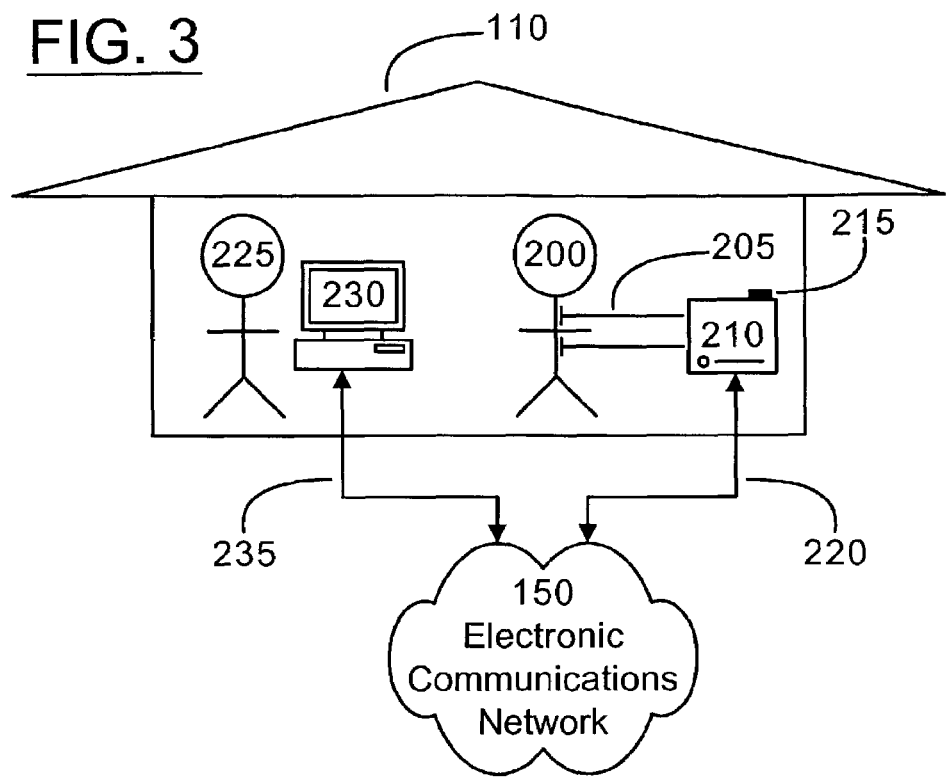
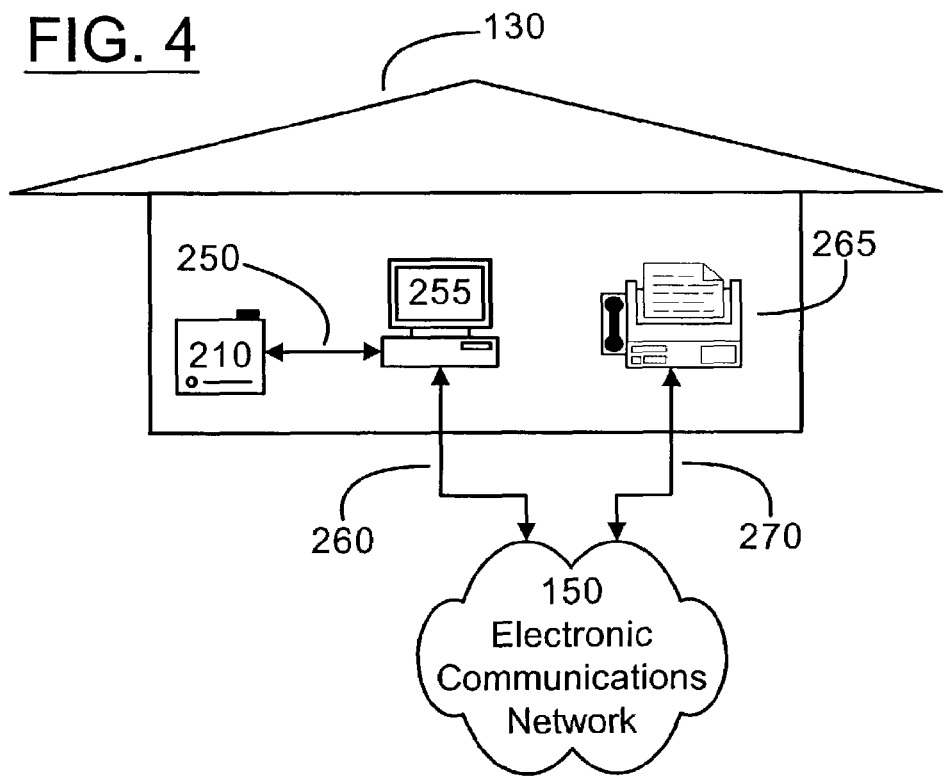

SERVICE CENTER SYSTEM AND METHOD AS A COMPONENT OF A POPULATION DIAGNOSTIC FOR SLEEP DISORDERS

CROSS-REFERENCES TO RELATED APPLICATIONS

Not applicable

STATEMENT AS TO RIGHTS TO INVENTIONS MADE UNDER FEDERALLY SPONSORED RESEARCH OR DEVELOPMENT

Not applicable

REFERENCE TO A "SEQUENCE LISTING," A TABLE, OR A COMPUTER PROGRAM LISTING APPENDIX SUBMITTED ON A COMPACT DISK

Not applicable

BACKGROUND OF THE INVENTION

The present invention generally relates to ways of monitoring health related disorders. More particularly, the invention provides a method and system for monitoring and controlling signals of sleep disorders acquired from a mammal user. Merely by way of example, the invention is applied using wide area electronic communication network and computer hardware. But it would be recognized that the invention has a much broader range of applicability such as applicability in an enterprise networks and others.

Many diseases afflict humans and other mammals. More than eighty such diseases comprise a class of ills known as sleep disorders. Some sleep disorders pose serious threats to health and well-being, and some are often treatable. Others are believed to be untreatable. As merely an example, sleep disorders are common. Many humans having a sleep disorder are often unaware of their affliction. For example, a single sleep disorder, obstructive sleep apnea, affects 5-15% of American adults and may be reasonably suspected in the 40% of adults who snore and the 5-10% of children who snore. Thus, obstructive sleep apnea is sufficiently common that, ideally, all primary care physicians should perform evaluations for it several times per day and should expect to diagnose it several times per week. Yet, fewer than 1% of patients in primary care carry the diagnosis of sleep apnea (E. M. BALL, et al. Diagnosis and treatment of sleep apnea within the community. The Walla Walla Project. Arch Intern Med. 1997;157(4):419-24.) (N. R. KRAMER, et al. The role of the primary care physician in recognizing obstructive sleep apnea. Arch Intern Med. 1999;159(9):965-8.) (N. C. NETZER, et al. Using the Berlin Questionnaire to identify patients at risk for the sleep apnea syndrome. Ann Intern Med. 1999;131(7):485-91.) (T. YOUNG, et al. Estimation of the clinically diagnosed proportion of sleep apnea syndrome in middle-aged men and women. Sleep. 1997;20(9):705-6.). A major limitation to reducing the public health burden of sleep disorders has been in diagnosing them.

Conventional techniques for diagnosing sleep disorders have limitations preventing them from becoming widely used. For example, if the patient's fundamental problem occurs during sleep, it often follows that observations should be made of the sleeping patient. Such observations are generally not practical in most physician offices. Specialized sleep-monitoring facilities allow assessments of a sleeping patient by collecting a plurality of physiological signals from the patient—a procedure known as "polysomnography." Polysomnography performed in such facilities, however, is often inconvenient for the patients who sleep there overnight and has proven to be expensive as well.

To overcome the limitations of dedicated sleep-monitoring facilities, other conventional techniques may permit collection of physiological signals as the patient sleeps at his or her home. These techniques include a hardware device for recording physiological signals. After recording physiological signals during sleep, the recorded physiological signals are accessed and analyzed, and information related to the analysis is made available to an end-user. Conventional techniques have many limitations in this regard. Logistics surrounding the analysis facility and return of the recording device are a major issue.

In some techniques, a physician's office or other health care facility is an analysis facility. This typically means that the expertise needed to analyze the signals resides within the health care facility. Humans may be the repository of such expertise, but this is problematic because humans ideally need training to performing such analyses, and because human experts are generally expensive. Machines (including software codes running on general purpose computers) may also perform analyses in one or more health care facilities. Such an arrangement places significant burdens on the human caretaker of the machine(s) at each facility. For example, a caretaker should be aware of updates and recalls of the analysis software, and should install updates as they become available. In addition, the caretaker should ensure the computer is properly configured for the software and remains in a validated state, all of which may be challenging, given periodic updates to operating systems, possible corruption of necessary system files, interference from other software, and so on. Physical and usage security also should be maintained around the computer, to prevent accidental or malicious tampering. This is especially difficult for a shared, general-purpose computer. Although some conventional techniques use both humans and machines to perform analyses, such techniques often magnify problems associated with a system, which inherits problems of both humans and machines.

Other approaches attempt to centralize the analysis facility. As merely an example, a company called Sleep Solutions Inc. (herein "Sleep Solutions") sends sleep-monitoring hardware to the patient's home by post or other delivery service. The hardware records physiological signals and is then returned, by post or other delivery service, to the Sleep Solutions analysis facility. The physiological data are analyzed, and the report is made available to the patient's physician over the Internet. There are several difficulties with this method. Postal services may be slow. Overnight delivery is possible with some delivery services, but at considerable expense. Furthermore, equipment may be damaged or lost in transit, which adds to expense and may necessitate a repeat study on the patient. This approach may also require considerable expense to support an infrastructure at the analysis facility to receive diagnostic hardware items, prepare them for the next use, and then distribute them. Still another limitation with the Sleep Solutions system arises in making patient reports available on the Internet. Any transmission of medical information must generally be done securely. Sleep Solutions employs the common combination of username and password at the end-user site. A limitation of this system is well known: many human computer-users have a tendency to choose an easily-guessed password and/or write their password somewhere it might be found.

Another product is offered by SNAP Laboratories, which also uses a centralized analysis facility. SNAP often uses a digital audio tape (DAT) recorder to capture the sounds made by a sleeping patient. The sounds are recorded onto a DAT cassette tape, and the cassette tape is sent by post or other delivery service to an analysis facility maintained by SNAP. This system has all the problems of the system of Sleep Solutions, and further adds costs of a consumable data storage item (the DAT cassette tape).

Other conventional approaches attempt to teach the transmission of physiological data to a remote analysis facility. These approaches, however, often cannot practically be implemented on a large scale, as they contain significant shortcomings, e.g. confidential patient information is open on the network, account information is inadequate, only a portion of information of potential diagnostic utility is transmitted, analysis methods are inflexibly implemented, provisions for technically unsophisticated users are not described, and so on. Depending upon the particular approach, there can also be many other limitations.

From the above, it is desirable to have improved techniques for monitoring health related disorders.

BRIEF SUMMARY OF THE INVENTION

According to the present invention, techniques for monitoring health related disorders are provided. More particularly, the invention provides a method and system for monitoring and controlling signals of sleep disorders acquired from a mammal user. Merely by way of example, the invention is applied using wide area electronic communication network and computer hardware. But it would be recognized that the invention has a much broader range of applicability such as applicability in enterprise networks and others.

In a specific embodiment, the invention provides a method for evaluating sleep disorders in mammals and distributing control information related to the sleep disorders through electronic communication networks. The method includes acquiring analog information related to physiological signals through a mobile device from a mammal user. The mammal user is at a geographic location outside of a sleep laboratory staffed by trained technicians (e.g., conventional location for treatment by trained technicians and physicians). The mobile device is coupled to one or more sensing devices, which is/are coupled to one or more monitoring regions of the mammal, e.g. neck, pericardium, suprasternal notch, scalp, etc. The method includes converting the analog information into a digital format using a signal processing device and transmitting information related to the physiological signals in the digital format to one or more service computers through an electronic communications network. Each of the service computers is operably coupled to a health information control facility. Alternatively, one or more of the service computers is coupled to the health information control facility. The method determines if the mammal user has related control information at at least one of the health information control facilities. The related control information is received through a communication network. The method processes the information related to the physiological signals at one or more of the service computers to provide a report associated with the information related to the physiological signals and the mammal user. The method communicates report information in the report associated with the information related to the physiological signals upon indication of receipt of at least control account information of the mammal user based upon the determining the related account information.

In an alternative specific embodiment, the invention includes a system for evaluating sleep disorders in mammals and distributing control information related to the sleep disorders through electronic communication networks. The system comprises one or more memories that include computer codes. A code is directed to acquiring analog information related to physiological signals through a mobile device from a mammal user, which is at a geographic location outside of a sleep laboratory staffed by trained technicians. The mobile device is coupled to one or more sensing device(s), which is/are coupled to one or more monitoring regions of the mammal. A code is directed to converting the analog information into a digital format using a signal processing device. A code is directed to transmitting information related to the physiological signals in the digital format to one or more service computers through an electronic communications network. Each of the service computers is operably coupled to a health information control facility. Alternatively, one or more of the service computers is coupled to the health information control facility. A code is directed to determining if the mammal user has related control information at one of the health information control facilities. A code is directed to processing the information related to the physiological signals at one or more of the service computers to provide a report associated with the information related to the physiological signals and the mammal user and a code is directed to communicating report information in the report associated with the information related to the physiological signals upon indication of receipt of at least control account information of the mammal user based upon the determining the related account information.

In an alternative specific embodiment, the invention provides a controlled method for evaluating sleep disorders in mammals and distributing information including case data related to the sleep disorders through communication networks. The method includes capturing analog information related to physiological signals through a remote device from a mammal user outside of a sleep laboratory staffed by trained technicians. The method also includes converting the analog information into a digital format using a signal processing device and transmitting information related to the physiological signals in the digital format to one or more service computers through an electronic communications network. The method includes transferring case data information related to the physiological signals to the service center receiving the physiological signals and processing the information related to the physiological signals at one or more of the service facilities to form an output associated with the information and the mammal user. A step of associating a portion of the case data information to the output associated with the physiological signals to form a report is included. The method communicates report information in the report derived from the information related of the physiological signals and case data.

In still an alternative specific embodiment, the invention provides a controlled system for evaluating sleep disorders in mammals and distributing information including case data related to the sleep disorders through communication networks. The system comprises one or more memories, which include computer codes. A code is directed to capturing analog information related to physiological signals through a remote device from a mammal user outside of a sleep laboratory staffed by trained technicians. A code is directed to converting the analog information into a digital format using a signal processing device and a code is directed to transmitting information related to the physiological signals in the digital format to one or more service computers through an electronic communications network. A code is directed to transferring case data information related to the physiological signals to the service center receiving the physiological signals. A code is directed to processing the information related to the physiological signals at one or more of the service facilities to form an output associated with the information and the mammal user. A code is directed to associating a portion of the case data information to the output associated with the physiological signals to form a report. The one or more memories also include a code directed to communicating report information in the report derived from the information related of the physiological signals and case data.

Various additional objects, features and advantages of the present invention can be more fully appreciated with reference to the detailed description and accompanying drawings that follow.

BRIEF DESCRIPTION OF THE DRAWINGS

FIG. 3 shows a configuration of a patient home according to an embodiment of the present invention.

FIG. 4 shows a configuration of an end-user facility according to an embodiment of the present invention.

DETAILED DESCRIPTION OF THE INVENTION

Figure 1:
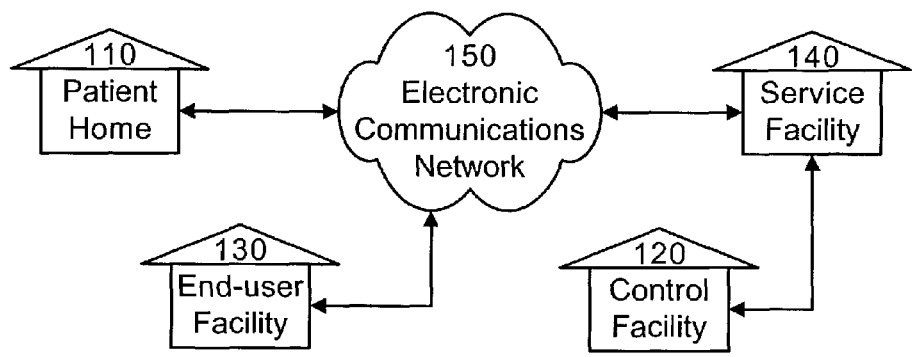
FIG. 1 shows a simplified diagram of a method for communicating sleep-related data according to an embodiment of the present invention.

According to the present invention, techniques for monitoring health related disorders are provided. More particularly, the invention provides a method and system for monitoring and controlling signals of sleep disorders acquired from a mammal user. Merely by way of example, the invention is applied using wide area electronic communication network and computer hardware. But it would be recognized that the invention has a much broader range of applicability such as enterprise networks and others.

We have discovered that few diagnostics have been successfully applied on a scale as massive as the one demanded for sleep disorders. Such wide spread diagnostics are termed "population diagnostics." Examples of successful population diagnostics include, but are not restricted to, the blood pressure cuff (sphygmomanometer), the thermometer, and the weight scale. Population diagnostics are often not routinely applied by physicians, but by ancillary healthcare personnel, such as nursing assistants and the like. Accordingly, performance requirements for a population diagnostic are more stringent that requirements for diagnostics used in less massive numbers. Table 1 shows a partial list of characteristics we found in effective population diagnostics.

TABLE 1—CHARACTERISTICS OF A POPULATION DIAGNOSTIC

Inexpensive:
(a) Equipment (hardware and software) should be inexpensive to acquire (e.g., easily affordable to a primary care physician's practice);
(b) Per-use cost is low (e.g., a few U.S. dollars at this time) in materials and staff time;
(c) Simple to train ancillary personnel to perform the diagnostic.

Foolproof (i.e., yield trustworthy results almost 100% of the time it is applied):
(a) Few, if any, demands on the patient;
(b) Few, if any, demands on the staff;
(c) Reliable and durable.

Unobtrusive, meaning:
(a) Low-maintenance
(b) Minimal administrative overhead.
(c) Minimal data management overhead.
(d) Not require manually-performed updates or modifications once installed.

Results should be quick (i.e. best available in near real time, at the point of care).

Results must be understandable to the end-user.

Safe.

Reasonably accurate.

To achieve some or all of the above, the present invention provides a novel "sleep-data service center" (henceforth "service facility" or "service center") that communicates electronically with end-user facility(s) and/or the patient's home. In addition to physiological data, such communication includes, but is not restricted to, administrative data, physiological meta-data, clinical data, and several other data types described below. A plurality of data types allows the sleep-data service center to perform many functions of value for both the patient and the end-user(s). A plurality of service functions, in combination with the ease of communication between two or all parties, is a highly desirable step in developing a population diagnostic for sleep disorders. The invention also provides a "health information control facility" (henceforth "control facility") which provides information to the service facility, enabling the service facility to dispense services in a disciplined and regulated manner. The control facility can be a third party facility, which is independent, in some embodiments. Alternatively, the control facility can be integrated with the service facility in other embodiments. Of course, there can be other ways of carrying out the functionality described herein. Further details of the present invention can be found throughout the present specification and more particularly below.

FIG. 1 shows a simplified diagram of a method according to an embodiment of the present invention. This diagram is merely an example, which should not unduly limit the scope of the claims herein. One of ordinary skill in the art would recognize many other variations, modifications, and alternatives. As shown, physiological signals and other data are acquired in patient home 110. The signals, data, and/or data derived thereof are transmitted from the patient home to one or more service facilities 140 via an electronic communications network 150. Service facility 140 provides one or more services to one or more end-users located at end-user facility 130. As part of some services, service facility 140 sends information to the end-user 130 via an electronic communications network 150, which may or may not be the same communication network by which service facility 140 received data. Actions of service facility 140 may be modified by information received from health information control facility 120, which is operably coupled to service facility 140 and may optionally communicate to external entities and facilities via electronic communication network 150.

Preferably, patient home 110 represents any facility that is not a sleep laboratory staffed by trained sleep technicians ("trained" as defined by the American Sleep Disorders Association). It is generally intended to represent any facility in which the patient may sleep in the due course of their life, e.g. the patient's home, a hotel room, the home of another person, the bunk of a tractor-trailer cab, a ship's cabin, an aerospace vehicle, a hospital bed in a general medical ward, a hospital bed in an intensive care unit, a nursing home, a skilled nursing facility, a research study site, a primary care physician's office where a nap opportunity may be afforded without the presence of a trained sleep technician, and so on.

Typical physiological signals collected in the home for the purpose of diagnosing sleep disorders include, but are not restricted to, electroencephalographic signals; electrocardiographic signals; electromyographic signals; electrooculographic signals; signals derived from movements of the chest, abdomen, or limbs; signals derived from body position, oximetry, penile tumescence, temperature; sound; and video.

The physiological signals and/or data derived from the original data are hereinafter collectively referred to as "physiological data," no matter when, where, how, or how often transformation of signals or data occurs. Likewise, data derived from data are still termed "data."

The communication network 150 may be composed of one or more electronic networks, for example, the Internet, some other wide area network, a local area network, the telephone system, a wireless system, power lines, a cable television network, a satellite network, and so on. Preferably, electronic communications network 150 is not a single fixed network, but may represents many or all types of electronic communications networks over which entities may communicate at any time. Thus, even if two entities are communicating over one network at one instant and another network at another instant, for purposes here, they will be said to be communicating over communications network 150 at both times.

Each facility shown in FIG. 1, i.e. patient home 110, end-user facility 130, control facility 120, and service facility 140 is a logical entity. That is, each may be composed of zero or more physically distinct facilities and need not be fixed sites, although their functionalities will always be present. The exceptions are: (a) at least one physically distinct service facility 140 is electronically connected to at least one physically distinct end-user facility 130 via electronic communications network 150, and (b) at least one service facility 140 is operably coupled to at least one control facility 120. Thus, multiple configurations are possible; one example according to the present invention is shown in FIG. 2.

Figure 2:
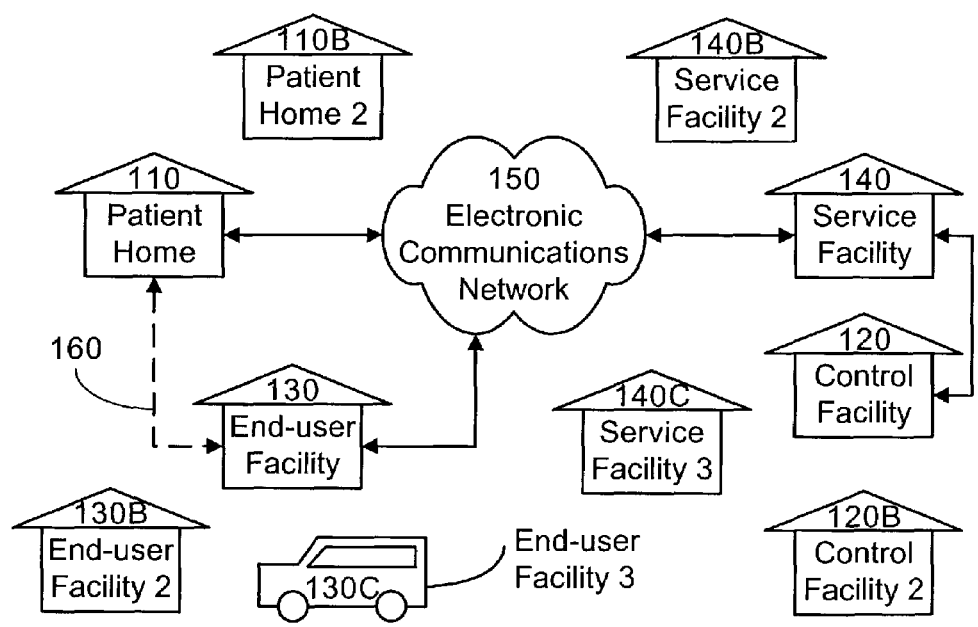
FIG. 2 shows a configuration of facilities and electronic communication links according to an embodiment of the present invention.

Except for the two linkages mentioned above, any facility may communicate with any other facility via communications network 150, via a different electronic communications means, or (as shown in FIG. 2) may not communicate electronically at all. In particular, it is possible that patient home 110 may not communicate electronically with another facility. In such a case, physical transmission step 160 may move data from patient home 110 to end-user facility 130, followed by electronic communication of data from end-user facility 130 to service facility 140 via communication network 150. Merely by way of example, physical communications step 160 may involve a human carrying the data from one facility to another, the data being stored in some device or devices in certain embodiments.

Other entities (not shown) may be in electronic communication with entities shown in FIG. 2. For example, a bank or an insurance company may communicate with the end-user facility. In addition, there may be multiple end-users, e.g. a primary care physician, a specialist physician, a researcher, a transportation regulatory agency, and so on, each of which may have their own facility(s) or shared facility(s).

In an alternate embodiment, the patient is the end-user. Thus, patient home 110 is combined with end-user facility 130 into a unified facility (not shown). Such unified facility electronically communicates with service facility 140 via communications network 150. FIG. 2 is also an example, which should not unduly limit the scope of the claims herein. One of ordinary skill in the art would recognize many other variations, modifications, and alternatives. Additional details of the invention are provided throughout the present specification and more particularly below. FIG. 3 shows further details of patient home 110 according to an embodiment of the present invention. The figure is merely an example, which should not unduly limit the scope of the claims herein. One of ordinary skill in the art would recognize many other variations, modifications, and alternatives. Mammalian patient 200 is monitored by one or more physiological sensors 205 in patient home 110. Physiological sensor(s) 205 supply data to data marshaling device 210. A plurality of data and software codes (not shown) may reside on data marshaling device 210. Optionally, mammalian patient 200 may supply para-physiological data to data marshaling device 210. As an example of para-physiological data, mammalian patient 200 may activate optional event marker 215 on data marshaling device 210. As another example of para-physiological data, a microphone may capture patient's vocalized memo while event marker 215 is activated.

At various times, or continuously, data marshaling device 210 transmits accumulated data from patient home 110 to service facility 140, via electronic connection 220 and communications network 150. Electronic connection 220 may be nothing more than a cable or cables, a cable jack, an infrared beam, and so on. As described later, data marshaling device 210 may transmit one or more data classes in addition to physiological data and optional para-physiological data. In an alternate embodiment, data marshaling device 210 may connect with communications network 150 via a connection (not shown) with network interface device 230.

In another alternate embodiment, electronic connections 220 and/or 235 to communications network 150 are absent in patient home 110. In this embodiment, data marshaling device 210 records data, and is later physically transported to another facility where data marshaling device 210 is electronically connected, directly or indirectly, to communications network 150. For example, data marshaling device 210 may be physically transported 160 to end-user facility 130, where it is electronically connected to communications network 150. Once connected to communications network 150, data recorded on data marshaling device 210 may be transmitted to service facility 140. Alternatively, data marshaling device 210 may have one or more removable components capable of storing data, e.g. floppy disk, PCMCIA card, Smart Media®, Memory Stick®, SanDisk®, and the like. These removable components may be transported within a facility or between facilities. These removable components may then be coupled to some device that is, in turn, coupled to electronic communications network 150 in some embodiments.

Optionally, interested party 225 is a human that is interested in the health or well-being of mammalian patient 200. Interested party 225 and mammalian patient 200 may or may not be the same person, and they may or may not be located at the same facility. For example, interested party 225 may be parent, bed-partner, caretaker, friend, relative, or physician of mammalian patient 200. FIG. 3 depicts the case in which interested party 225 and mammalian patient 200 are separate mammals located at the same facility. Interested party 225 interacts with network interface device 230, which may be, for example, a personal computer, a telephone, a personal digital assistant, and so on. Network interface device 230 is electronically connected 235 to communications network 150.

In an alternate embodiment, data marshaling device 210 and electronic interface device 230 are the same device (not shown), having all necessary characteristics of each separate device. In an additional alternate embodiment, data marshaling device 210 connects to communication network 150 via an intermediate connection (not shown) with an electronic interface device 230. FIG. 4 shows further detail of end-user facility 130 according to an embodiment of the present invention. The figure is merely an example, which should not unduly limit the scope of the claims herein. One of ordinary skill in the art would recognize many other variations, modifications, and alternatives. Data marshaling device 210 can be electronically linked 250 to network interface device 255, which may be a desktop computer, personal digital assistant, telephone, specialized hardware, etc. Network interface device 255 is electronically connected 260 to communications network 150.

Figure 5:
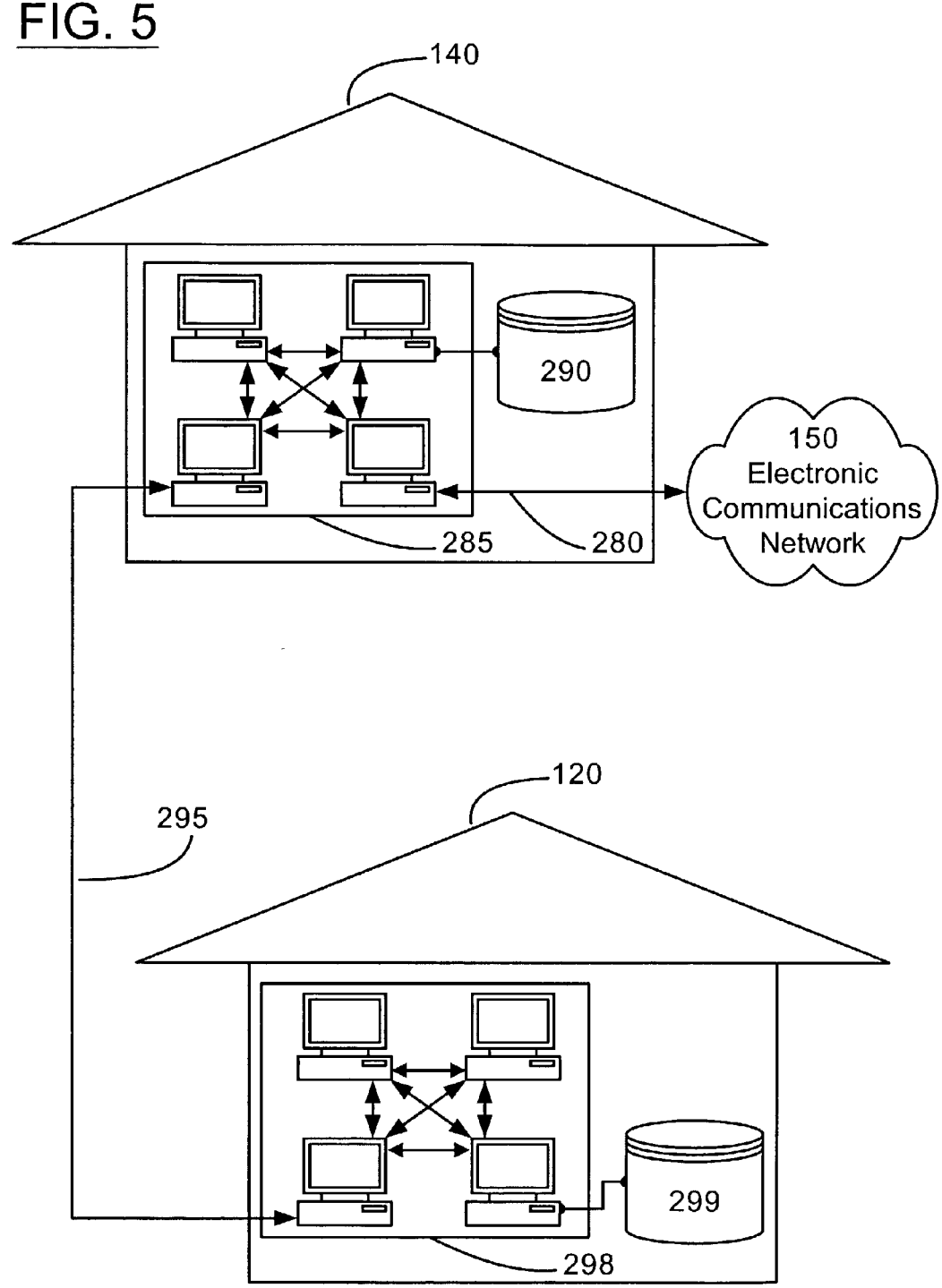
FIG. 5 shows a configuration of a service facility and control facility according to an embodiment of the present invention.

End-user facility 130 optionally also contains one or more report-rendering devices 265 electronically connected 270 to communications network 150. Report-rendering devices 265 may be identical to network interface device 255, may be a component of network interface device 255, or, as shown, may be distinct from it and electronically connected to it through communications network 150 or some other means. Report-rendering device 265 may be a general-purpose desktop computer, a personal digital assistant, a telephone, facsimile machine, printer, video monitor or television, loudspeaker, gaming unit, special purpose hardware, and so on. As noted earlier, patient home 110 and end-user facility 130 may be the same site when the patient is the end-user. In an alternate embodiment, data marshaling device 210 connects directly to communication network 150, as in FIG. 3. FIG. 5 shows further detail of service center 140 and control facility 120 according to an embodiment of the present invention. The figure is merely an example, which should not unduly limit the scope of the claims herein. One of ordinary skill in the art would recognize many other variations, modifications, and alternatives. Communications network 150 is electronically linked 280 to a network of computers 285 in the service facility 140. The network of computers 285 may be composed of one or more computing devices, as is widely practiced in the art. A plurality of different network arrangements are possible, not all components necessarily being connected simultaneously. The arrangement shown is for example only and is not meant to restrict the various embodiments possible. It is further understood that the spirit of this embodiment also includes computing devices separated by a short distance, such that electronic media may be physically transported between them by a walking human, pneumatic message tube, or other convenient means. One or more data repositories 290 reside on computing devices that are part of, or are operably coupled to, network of computers 285. All service facilities 140 need not contain a data repository 290. Data repositories 290 contain one or more data elements, possibly, but not necessarily, falling into one or more of the data classes shown in table 2a. Descriptors of the patient and/or the diagnostic test are called "patient data." Patient data is itself composed of a plurality of data classes, shown in table 2b. In a specific embodiment, "Case data" refers to the aggregation of all data classes comprising patient data, excepting physiological data, although other definitions can also exist.

TABLE 2a

Examples of Sleep-Related Data resources,
patient data,
    physiological data,
    case data,
queries,
end-user data,
end-user supply data,
end-user preferences,
service data and test parameters TABLE 2b Examples of Patient Data

| Data Class | Example(s) |
| --- | --- |
| Physiological data | electroencephalographic data; electrocardiographic data; electromyographic data; electrooculographic data; data derived from movements of the chest, abdomen, limbs, other body parts, or the body as a whole; data derived from body position, oximetry, penile tumescence, temperature, and usage of therapeutic devices such as continuous positive airway pressure (CPAP); sound, including audible sound, doppler flow data, and ultrasound; and video. Derived data, such as Bispectral Index ®, too. |
| Para-physiological data | activation of event marker, recording of event memos, sleep log |
| Physiological meta-data | montage data, clock time, time of recording start(s) and stop(s), parameters used for amplification or filtering or digitization, error or warning notifications |
| Service data | list of services the service center should provide; list of analyses to be run; values for synchronizing clock on |

TABLE 2b-continued

Examples of Patient Data

| Data Class | Example(s) |
| --- | --- |
| Configuration data | data marshalling device; manually programmed montage serial number of data recording device, version number of firmware operating on data recording device, checksums of firmware instructions |
| Clinical data | age, sex, height, weight, blood pressure, symptoms, medical history (including co-morbid conditions, past medical history, medication history, surgical history, family history, social history, etc.), physical examination findings, laboratory and imaging findings, as well as derived or calculated values such as body mass index or scores on instruments such as the Epworth Sleepiness Scale, Stanford Sleepiness Scale, SF-36, Minnesota Multiphasic Personality Inventory, Beck depression inventory, Prime-MD, and so on. |
| Administrative data | patient identifiers such as name, social security number, driver's license number, medical history number, passport number; patient contact information; identifier for affiliated third parties such as physician medical practice, insurance company, or other third-party payor; identifiers for third-party programs such as insurance policy identifiers; procedure data |

TABLE 2b-continued

Examples of Patient Data

| Data Class | Example(s) |
| --- | --- |
| | such as CPT codes, LOINC codes, HCPCS, etc.; payment account identifiers such as credit card number, checking account number, PayPal identifier, identifiers referencing a line of credit at a service center, etc. |
| Authentication data | username, password, physical token identifier, or biometric identifier (possibly physiological) |

Tables 2a and 2b are merely examples, and are not meant to be exhaustive. Note that some data fall into more than one data class. For example, a checksum of firmware instructions may be in both the configuration data class and the authentication data class. A plurality of software codes resides on the network of computers 285. These codes, possibly in concert with data repositories 290 and possibly in concert with one or more humans, perform one or more services for the end-user(s). Such services may be delivered to end-user via electronic transmission and/or other means. Table 3 lists examples of services provided to end-user(s). Note: although services are performed by network of computer 285 within one or more service facilities, we will, for simplicity, sometimes refer to service center(s) 140 as providing service(s).

TABLE 3

Examples of Services Available to End-user(s)

| Name of Service | Action |
| --- | --- |
| Analysis | Identify, characterize, and/or tabulate physiological events by processing physiological data, possibly in conjunction with other data |
| Archive | Data management functions such as long-term storage, making backups, and the like |
| Authentication | Establish identity and/or role of end-user, patient, interested party, or other entity. |
| Interview | Collect selected non-physiological data, e.g. clinical data, administrative data, etc. |
| Resource | Identify resources relevant to a specific set of data |
| Summary | Summarize data across multiple patients |
| Monitor | Monitor function of hardware, software, and/or patient in real-time, before and/or during and/or after a test |
| Billing | (1) Submission of electronic claims to third-party payors, and/or (2) Prepare documents to assist physician office in securing reimbursement (such documents may include HCFA form 1500, letter of medical necessity, claim forms, etc.), (3) Electronic funds transfer and/or credit card transaction. |
| Alert | Deliver urgent communications from service facility to end-user |
| Supply management | Track usage of consumable items such as disposable sensors; accept and confirm orders for supplies; coordinate shipping of supplies |
| Customer support | Provide help to end-user |
| Community | Facilitate communication between end-users around common topic(s) |
| Programming | Pro rammin the data marshallin device |
| Email | Electronic mail between various entities; in some situations, the real-world identity of an entity may be unknown to other entities |
| Account management | Tabulate and report usage statistics; management of password and other authentication information; user account creation, deletion, and other management functions such as maintaining contact information, assigning roles, etc. |
| Update | Determine and possibly install updates to software of data marshalling device, network interface device, network gateway |

TABLE 3-continued

Examples of Services Available to End-user(s)

| Name of Service | Action |
|---|---|
| | device, or possibly other device(s). May draw on monitoring and programming services. |
| Tracking | Log hardware that has been stolen, lost, recalled, expired, tainted, returned, destroyed, repaired, etc. |

Service facility 140 is operably coupled 295 to control facility 120. In one possible embodiment, control facility 120 includes network of computers 298 electronically coupled to data repository 299. Note: although services are performed by network of computer 298 within one or more control facilities, we will, for simplicity, sometimes refer to control center(s) 120 as providing service(s).

In addition to the data classes shown in tables 2a and 2b, "control information" constitutes a further data class. Control information enables service facility 140 to control access to the services it provides. For example, when service facility 140 provides the analysis service, it may be desirable for the service facility to control the circumstances under which the service is actually provided to end-user. The behavior of such controls may depend on zero or more pieces of information, examples of which are shown in table 4.

TABLE 4

Examples of Control Information and Control Decisions

| Control Information | Control Decisions |
|---|---|
| Hardware serial numbers | Block service if hardware has been recalled, reported stolen, etc. (Hardware serial numbers may be associated with data marshalling device 210, for example.) |
| Software version number | Block service if software version is obsolete, recalled, etc. (Software version numbers may be associated with software codes that run on network interface device 230, for example. Invention may possibly offer option to update software.) |
| Medical license number | Permit service if end-user is a licensed physician (e.g. federal law may prohibit performance of certain services, except under the prescription of a physician). Permit service if medical license is in good standing (licenses may expire, be revoked, etc.). |
| Payment account number | Permit service if valid and sufficient information is provided to extract payment. (Control information may include, in this example, a credit card number, an identifier for a deposit account that end-user maintains with service provider, a checking account number, a PayPal account identifier, and so on.) |
| Authentication data | Permit service if the service request is properly authenticated (e.g. with a password that is linked to the serial number of the hardware). |

Notice that control information may be drawn from a variety of data classes listed in tables 2a and 2b, or from other data classes or elements. Control information may be primarily associated with mammalian patient 200, with interested party 225, with end-user, or with other entity or entities. Control information may be secondarily related to mammalian patient 200 if it is associated with an entity that is associated with mammalian patient 200. Note also that control information may include sensitive information that may require a higher degree of confidentiality, e.g. payment codes and authentication data. Thus, optionally separating the control facility from the service facility may offer security advantages. Table 4 is merely an example.

It is understood that any electrical connection referred to herein may be a physical connection employing electronic or optical cabling, or a wireless connection employing electromagnetic radiation of any type, e.g. radio frequency radiation, infrared light, visible light, etc. Nothing in the invention prohibits non-electronic communication between entities, e.g. transmission of hard-copy confirmations by postal or courier service, or transmission of electronic items by non-electronic means (e.g. hand-carrying removable electronic storage media such as a floppy disk).

According to a specific embodiment, sleep-related data are collected from one or more sources, and are transmitted electronically from patient home 110 or end-user facility 130 to service facility 140 according to embodiments of the present invention. Merely by way of example, we have provided selected methods according to the embodiments of the present invention below.

Figure 6:
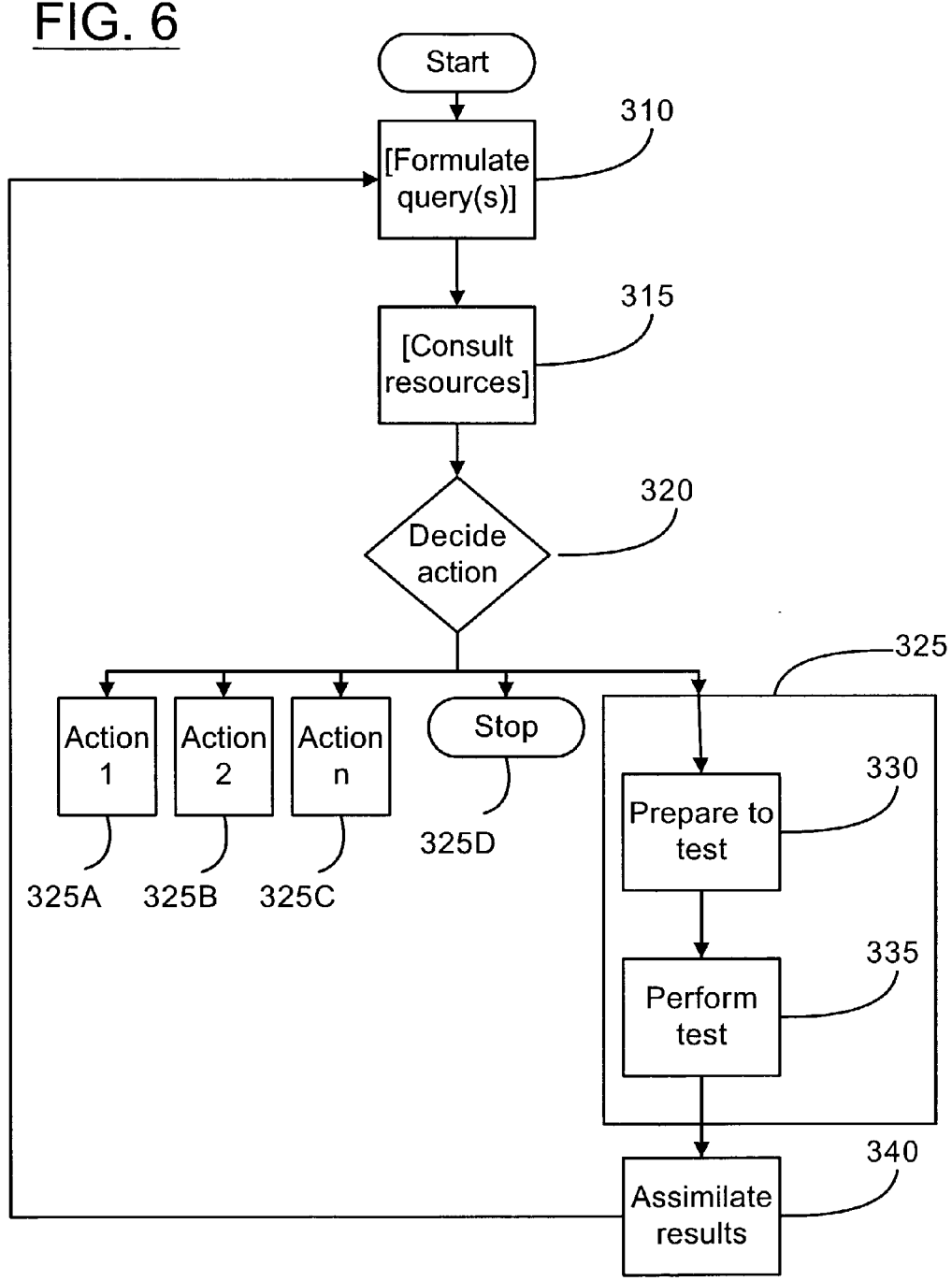
FIG. 6 shows a simplified overview of a method according to an embodiment of the present invention.

FIG. 6 shows simplified methods according to embodiments of the present invention. The figure is merely an example, which should not unduly limit the scope of the claims herein. One of ordinary skill in the art would recognize many other variations, modifications, and alternatives. In optional step 310 interested party 225 formulates one or more queries about mammalian patient 200. Such queries may be purely mental, or may be recorded in various ways. Examples of queries include, but are not restricted to, "Is my husband's snoring dangerous?" or "How should I evaluate hypersomnolence in a 52 year old man having a body mass index of 33 kg/m/m?" or "What is the best sensor montage to use in testing patient John Jones?"

As noted earlier, interested party 225 may be the same person as mammalian patient 200. Also note, however, that interested party may switch from entity to entity during the course of the invention. For example, when mammalian patient is a child, interested party 225 in some steps is most likely to be a parent, and in other steps is most likely to be a physician. The invention provides resources that may aid interested party 225 in satisfying the query(s) formulated in step 310. The term "resources" applies to sources of information and/or other services. Examples of resources include, but are not restricted to: (a) Articles from scientific or popular sources that are applicable to the diagnostic evaluation or to the management of sleep disorders; (b) Communities of interested parties; (c) Software codes that report the result of calculations or inferences made on the basis of data; (d) Advertisements from companies wishing to influence the buying decisions of interested parties; and (e) Indexes of resources.

In step 315, interested party 225 may optionally consult such resources. It is not expected that all possible queries in step 310 will be addressed by resources available in step 315. After consulting resources (step 315), interested party 225 may return to step 310 by formulating additional query(s). Alternatively, after consulting resources (step 315), interested party makes a decision on what to do next (step 320). This step 320 occurs whether or not one or more queries were formulated (step 310) or whether or not resources were consulted (step 315). One or more actions (325, 325A, 325B, 325C) may result from the decision (or decisions) made in step 320. For example, interested party may decide to consult a physician, or may decide to get more sleep, or may decide to exercise more, and so forth. Alternatively, interested party 225 may decide not to take any further action at all related to the invention (325D).

A possible action 325 resulting from decision 320 is to perform a sleep-related diagnostic test on mammalian patient 200 using aspects of the present invention. The diagnostic test includes two steps, preparing to test (step 330) and performing the test (step 335).

After diagnostic test 325 has been performed, interested party 225 assimilates (step 340) the results of the test. In many cases, this will lead to additional queries (e.g. "How should the newly-diagnosed sleep disorder be treated?"), and interested party returns to step 310. Even if the results of the diagnostic test 325 do not generate queries, steps 310 and 315 are optional, so step 320 is eventually reached, after which interested party may stop. Nothing in the invention precludes the performance of all steps in real time. We now turn to step 315, consulting resources. In an exemplary embodiment of the invention, resources are indexed or contained in one or more data repositories 290 connected to electronic communications network 285 at service facility 140. Resources are accessed by interested party 225 using network interface device 230. Interested party 225 may be located at any facility, so long as there is an electronic connection between network interface device 230 and network of computers 285. Because interested party 225 may be an end-user for some services, we will henceforth use the more general term "end-user."

Figure 7:
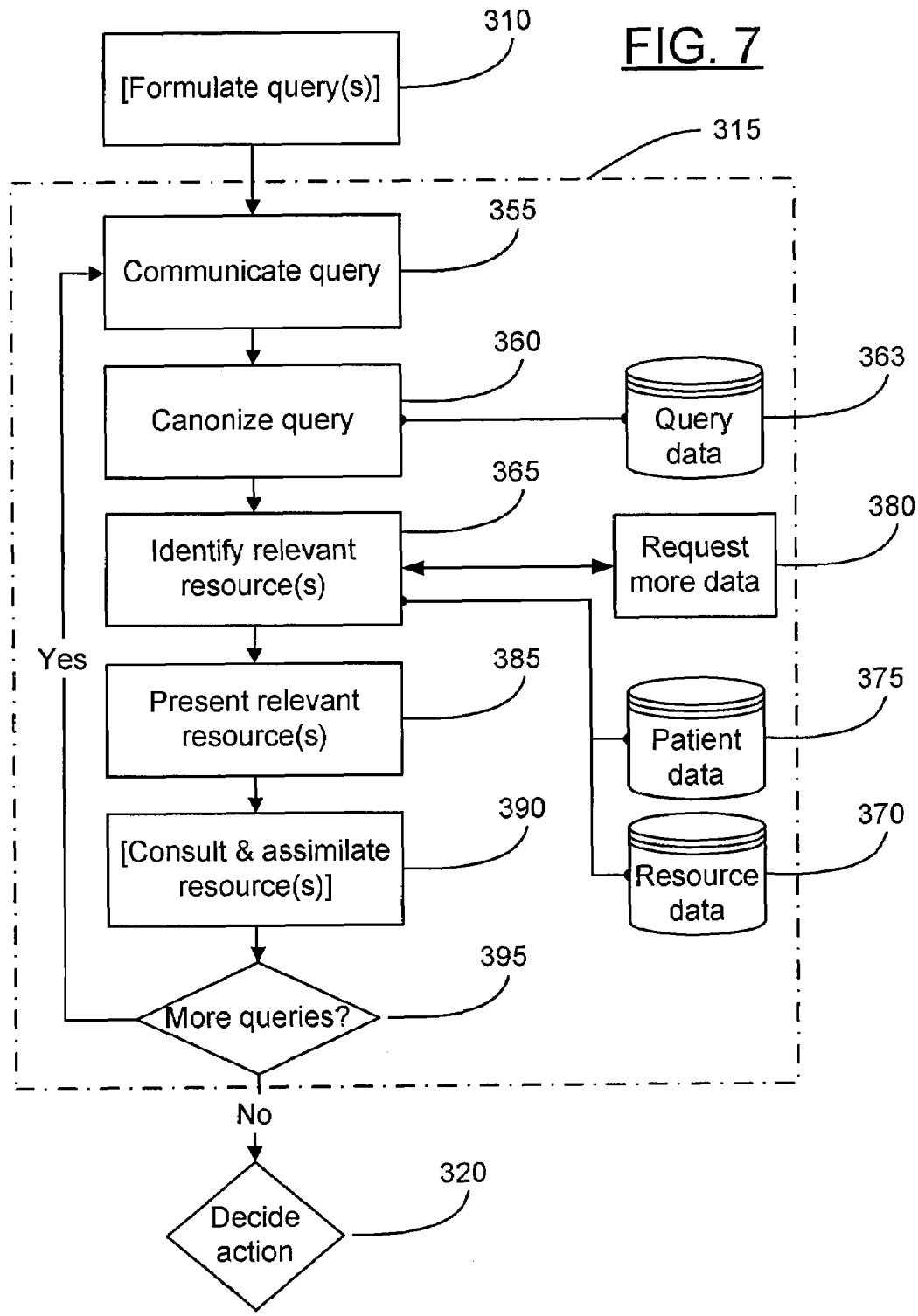
FIG. 7 shows details of the "Consult resources" function according to an embodiment of the present invention.

FIG. 7 shows details of step 315, in which end-user consults resources to answer one or more queries formulated in step 310. The figure is merely an example, which should not unduly limit the scope of the claims herein. One of ordinary skill in the art would recognize many other variations, modifications, and alternatives. Having formulated a query (step 310), end-user communicates the query (step 355) to network of computers 285. Software codes on network of computers translate the query (step 360) into a "canonical" form that can be readily manipulated by various software codes. As an example of canonization step 360, a database of canonical queries 363 may be searched by end-user to find the canonical query most closely matching the query formulated in step 310, e.g. by using Internet "FAQ" web pages as an interface to the database. As a further example, end-user may communicate the query 310 by typing or speaking or writing or signing it; software codes 360 may then select one or more possible canonized queries and possibly ask end-user to pick one or more. Thus, step 360 may involve bi-directional communication between network of computers 285 and end-user.

Next, in step 365 a canonical query identified in step 360 is matched against a database of resources 370, the result being zero or more resources deemed relevant to the canonical query. In cases where the canonical query is being applied to a specific patient population (whether an actual patient, a hypothetical patient, or a class of patients), data may be retrieved from a database containing data describing the patient(s) 375, such data becoming part of the criteria used to identify relevant resources 365. In some instances, patient database 375 may contain insufficient data to determine the relevance of a resource. In such instances, end-user may be asked to supply needed data. The relevant resources identified in step 365 are presented 385 to end-user, by various possible means, including electronically via network interface device 230, electronically by other means, through a mailed paper report, and so on.

Figure 8:
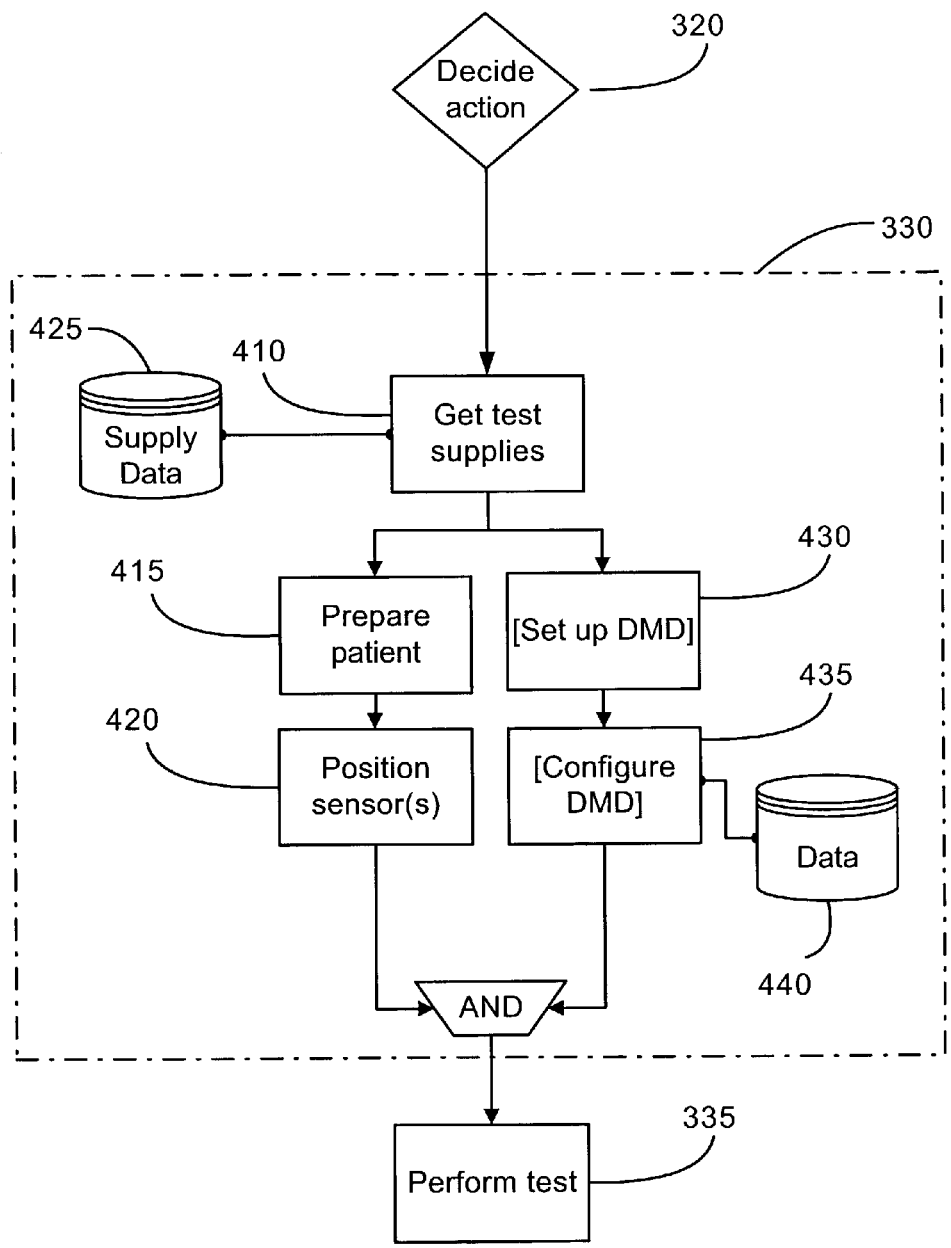
FIG. 8 shows details of the "Prepare to test" function according to an embodiment of the present invention.

End-user may ignore relevant resources or may consult them and possibly assimilate their contents (step 390). The consultation and assimilation steps may occur immediately or may be delayed. Should end-user have additional queries 395, the process 315 may repeat. Should end-user lack an additional query, end-user may decide upon some action 320. Consequences of step 315 may occur immediately or may be delayed. If end-user decides in step 320 to perform test 325, preparation 330 for test occurs next, as shown in FIG. 8. The figure is merely an example, which should not unduly limit the scope of the claims herein. One of ordinary skill in the art would recognize many other variations, modifications, and alternatives. In step 410, end-user obtains supplies needed to perform the test. Consumption of such supplies may be tracked by a supply database 425. Supply database may reside on network of computers 285, or it may reside elsewhere and optionally be in electronic communication with network of computers 285. In some embodiments, end-user may order supplies (not shown), such orders optionally using supply database 425. Data marshaling device 210 may be considered a supply item. Mammalian patient 200 may require preparation 415 for the test. For example, the patient may need instructions about the test, may need chest hair shaved, and so on. Some patients may be tested under specific circumstances, e.g. while undergoing a certain therapy, and those circumstances should so be established. The sensor(s) 205 to be used in the test are positioned 420 on or about the patient. In many instances, sensor(s) will be applied to various monitoring regions of the patient's body. In other instances, sensors may be placed in proximity to the patient (e.g. a video camera or a microphone, or even sensors embedded in a pillow or mattress). If a sensor is positioned on the patient, the act of positioning need not occur in patient home 110.

Data marshaling device ("DMD") 210, too, may need preparation for testing (step 430), e.g. insertion or checking of batteries. In certain embodiments, data marshaling device 210 stores digital codes, including software codes, operating parameters, patient data, and so on. Thus, in certain embodiments, data marshaling device 210 is configured with these digital codes (step 435), possibly in concert with data source 440. When such configuration is performed in association with information downloaded from service center 140, it is an example of the "programming service" of table 3.

Figure 9:
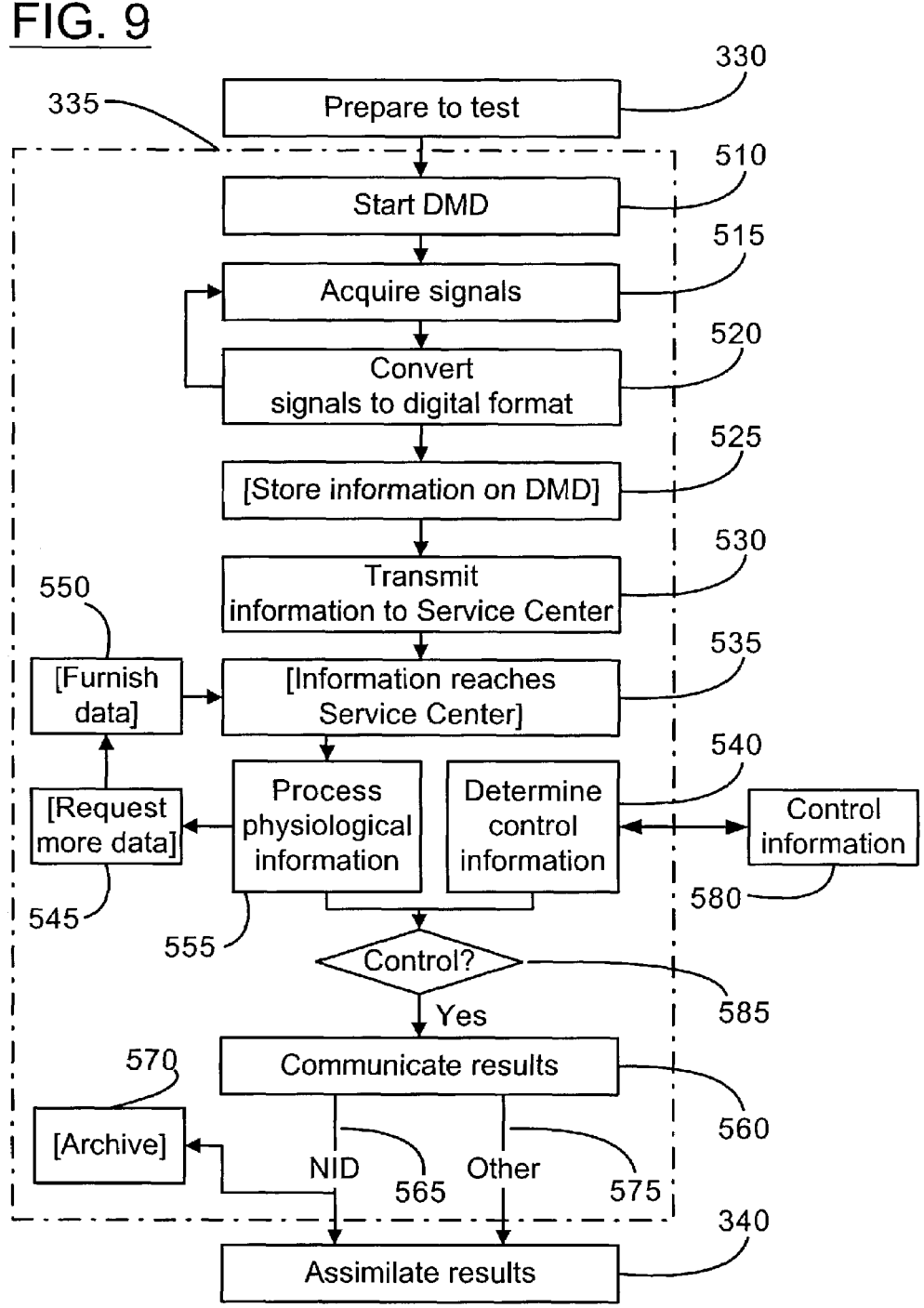
FIG. 9 shows details of the "Perform test" function according to an embodiment of the present invention.

With preparation of patient 200, sensor(s) 205, and data marshaling device 210, testing (step 335) of patient may begin. FIG. 9 shows details of performing test (step 335). The figure is merely an example, which should not unduly limit the scope of the claims herein. One of ordinary skill in the art would recognize many other variations, modifications, and alternatives. To begin, data marshaling device 210 begins operation (step 510). The device may be commanded or triggered to start by a mammal (e.g. with an on/off switch, a sensor-related action, or other mechanical, electrical, or other input. Alternatively, the device may have been configured to begin operation once a certain set of conditions occur (e.g. at a certain time).

Once operating, data marshaling device 210 acquires signals (step 515) in patient home 110, as transduced by sensor(s) 205. Data marshaling device 210 transforms signals into digitally-formatted data (step 520). This step may involve, for example, filtering, analog-to-digital conversion, and a host of other techniques known to persons with ordinary skill in the art.

Data marshaling device 210 may acquire non-physiological signals, e.g. para-physiological data corresponding to activation of even button 215 and/or data loaded as part of step 435. Thus, because data marshaling device 210 may contain information that could assist analysis of data derived from physiological signals, it may be more generally viewed as containing information related to the physiological signals.

In certain embodiments, information will be stored (step 525) on data marshaling device 210, for later retrieval. In these embodiments, information would be retrieved after an arbitrary period of time (microseconds, hours, days, etc.) and electronically transmitted to service center 140 in step 530. In other embodiments, information may be streamed to service center 140 as it arrives in data marshaling device 210 ("DMD"). Note that many embodiments widely regarded to stream data actually store data, for example, the sample-and-hold circuit of an analog-to-digital converter stores data for a period of time. In an exemplary embodiment of step 530, information stored on DMD 210 are uploaded to a personal computer, then transmitted over the Internet to service center 140 by the personal computer.

Information is transmitted to service center (step 530). To reach service center (step 535), information leaves electronic communications network 150, traverses electrical connection 280, and enters network of computers 285. Network of computers 285 may then process the information (step 555). In the event processing cannot be fully performed with the information that has arrived, network of computers 285 may request additional data (step 545). Data may be obtained by various means (step 550) and reach service center (step 535) where processing may again be attempted (step 555). Note that data may also be furnished (step 550) to service center 140 even when not specifically requested by step 545; this will be discussed later. Sensor(s) 205 may be removed from mammalian patient 200 after all physiological data have been stored on data marshaling device (step 525) or have been transmitted to service center (step 530).

Results of processing, whether intermediate or complete, are distributed to end-user(s) by a variety of means (step 560). However, at some point before results (often contained in a report) are communicated, the invention asserts control over the availability of processed results and/or archived data. Control is asserted by examination of control information 580 available from control facility 120. Control information 580 may reach control facility 120 by one or more paths, e.g. from a human interacting with a network interface device connected to electronic communications network 150, from DMD 210 connected to electronic communications network 150 via a network gateway device, from databases at local or remote sites, etc. The control information can be provided by an independent entity and/or an integrated entity. Service facility 140 determines (step 540) the available control information, then decides whether available control information permits communication of results (step 585). At a minimum, control information 580 should be present before results are communicated according to certain embodiments.

Results may be distributed (step 560) to end-user via network interface device ("NID") (step 565) connected to electronic communications network 150, e.g. a personal computer, a facsimile machine, etc. Results may optionally be archived on or through network interface device (step 570). Results may be distributed by other means (step 575), including, but not restricted to, paper-based reports sent through the mail.

Figure 10:
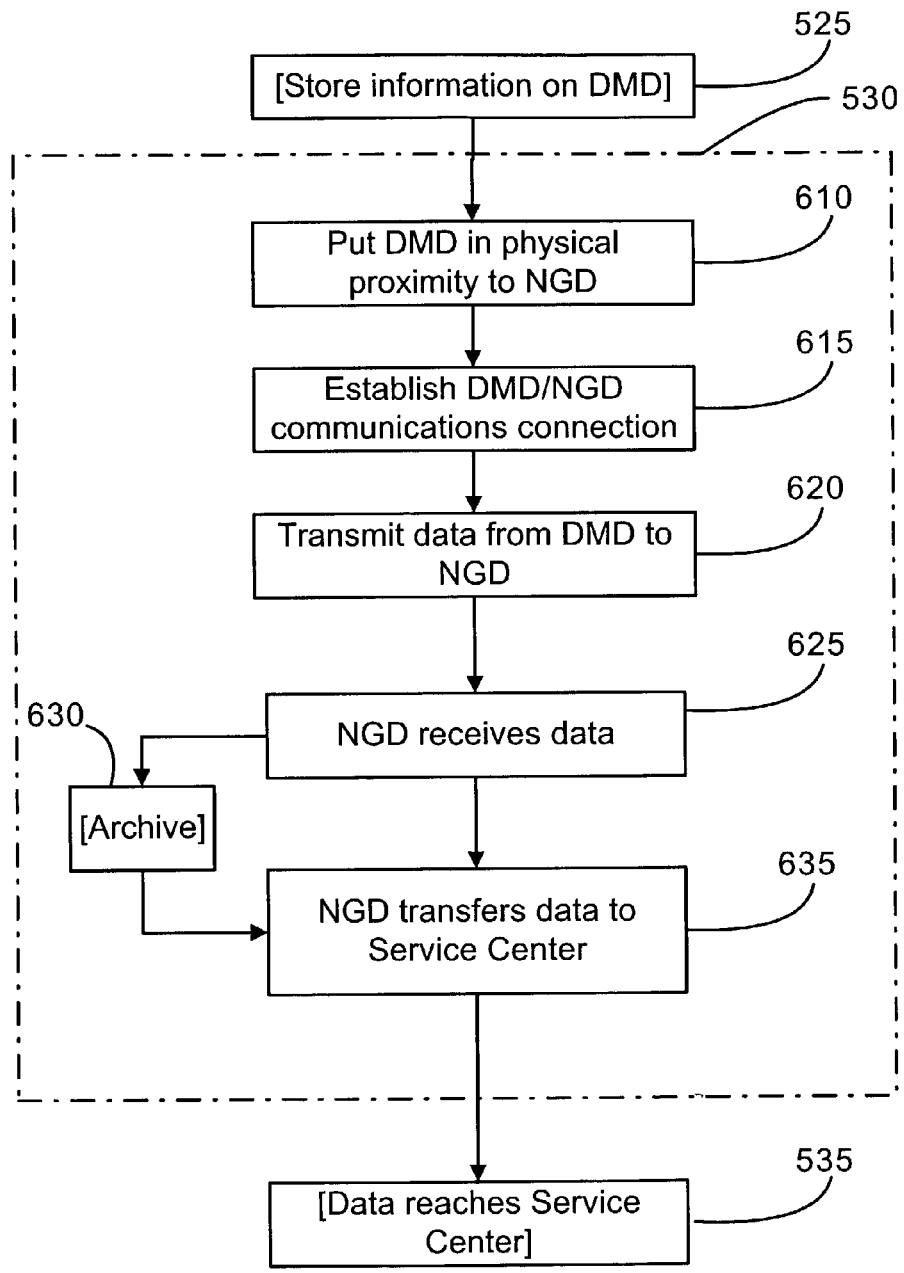
FIG. 10 shows details of transmitting information to service center according to an embodiment of the present invention.

FIG. 10 shows details of electronically transmitting data from data marshaling device 210 to service center 140 (step 530). The figure is merely an example, which should not unduly limit the scope of the claims herein. One of ordinary skill in the art would recognize many other variations, modifications, and alternatives. Data marshaling device 210 communicates with electronic communications network 150 via a network gateway device ("NGD"). There are a plurality of embodiments for network gateway device. For example, network gateway device may be network interface device 230 or 235. As a further example, network gateway device may be a modem built into data marshaling device 210, in which case step 610 (described below) is also built-in.

DMD and NGD are placed in physical proximity to each other (step 610) so that electronic communication between them may occur. The necessary degree of proximity will be determined by the nature of the communications link between DMD and NGD. In some embodiments, creating this proximity may involve moving DMD from one facility to another, as exemplified by step 160.

A communications connection between DMD and NGD is established (step 615). This may be done by a variety of methods well known in the art. Connection may occur, for example, over a cable, over a data bus, over a wireless link, over an infrared link, over an acoustic link, and so on. FIG. 4, for example, shows a connection 250 between DMD and network interface device 255. As a further example, DMD may connect to a personal computer using a cable plugged into the universal serial bus (USB) port of the personal computer. As an additional example, DMD may connect to a personal digital assistant by any of a variety of methods, as is well known to those of ordinary skill in the art. Establishing communications connection (step 615) may include protocols such as "handshaking" between DMD and NGD.

Data are transmitted from DMD to NGD (step 620) via the communications connection made in step 615. (Further details are given in FIG. 11.) NGD receives data (step 625) and transmits data to service center (step 635). NGD optionally archives some or all data in a non-volatile storage medium (step 630) for later retrieval. As noted earlier, "data" also refers to data derived from data. For example, data transferred from DMD to a personal computer via USB connection may be archived on the personal computer, then digitally filtered and rectified, and followed by transmission of the filtered and rectified data to service center. As a further example, data transmitted to service center in step 635 may be drawn from archive referenced in step 630.

Of note, data arriving at NGD in step 625 may arrive over a long period of time. Steps in FIG. 10 beyond 625 (i.e. steps 630 and 635) may await receipt of all data being transmitted, or may proceed after only a portion of data is received.

Figure 11:
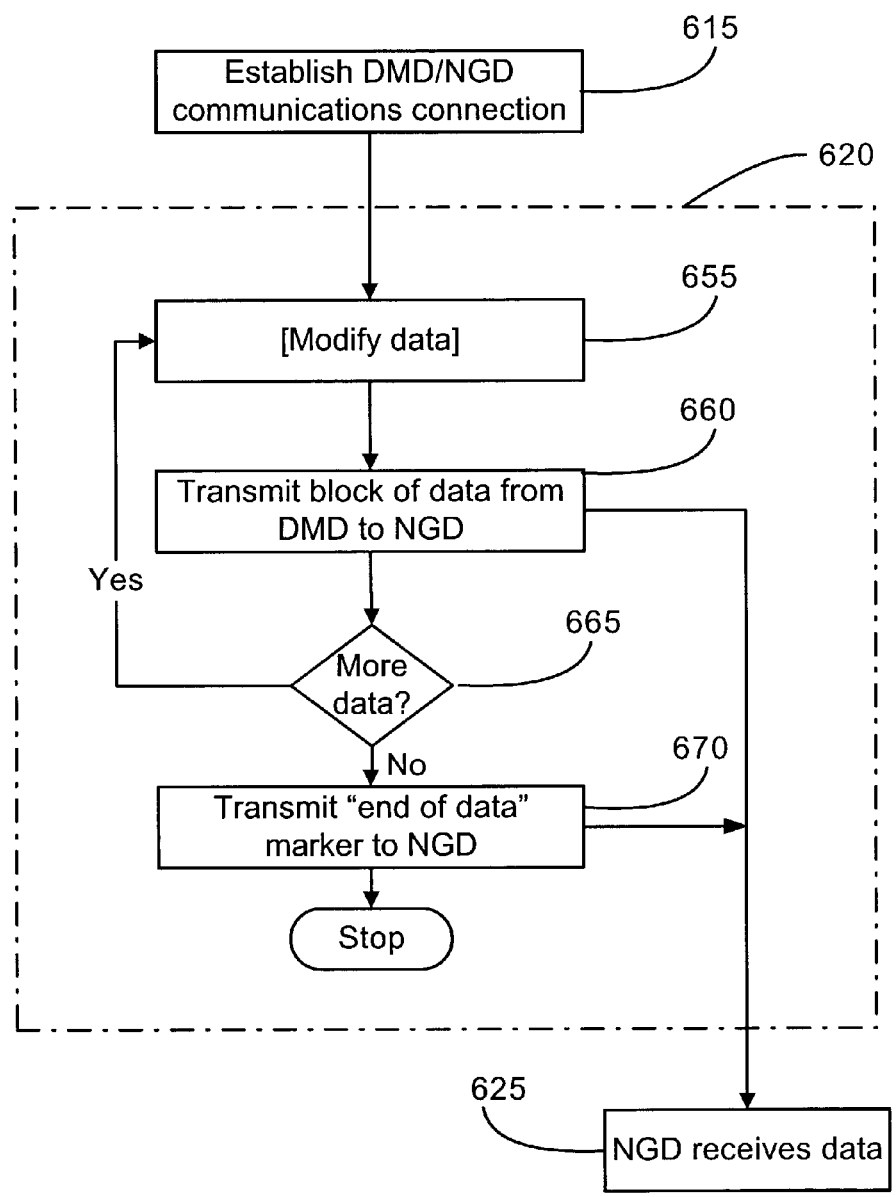
FIG. 11 shows details of transmitting information from data marshaling device to network gateway device according to an embodiment of the present invention.

Also note that there is nothing in the invention to prevent data from being stored on one or more removable components of DMD 210, e.g. a floppy disk, PCMCIA card, SmartMedia card, etc. A removable component may remain in place in DMD 210, or it may be removed and transported to another location where it may be enabled to communicate with NGD as described above. FIG. 11 shows details of electronically transmitting data from network gateway device (NGD) to service center (step 620). The figure is merely an example, which should not unduly limit the scope of the claims herein. One of ordinary skill in the art would recognize many other variations, modifications, and alternatives. Before data are moved from DMD to NGD, data are optionally modified (step 655). For example, a "header" may be attached to data (or a subset of data) by communications protocols such as TCP/IP or USB. As a further example, checksums may be computed for the data (or a subset of the data). As a further example, data stored on DMD may be permanently removed from storage on DMD as data are prepared to move to NGD. As a further example, a physiological signal may be digitally filtered. A data modification may optionally result in new data being stored on DMD.

Figure 12:
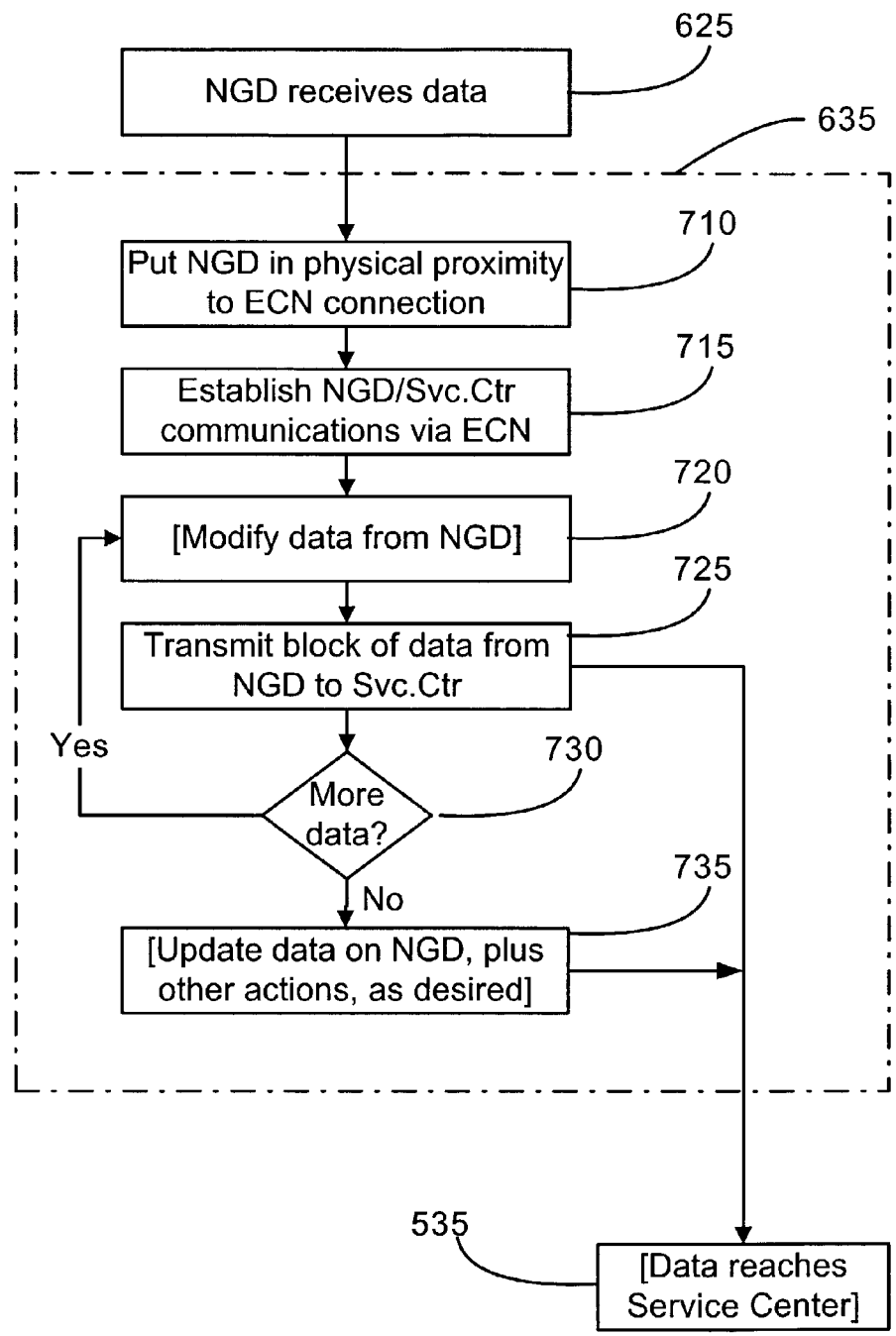
FIG. 12 shows details of transferring data from network gateway device to service center according to an embodiment of the present invention.

In one embodiment, the data (possibly of large size) on DMD are divided into smaller-sized blocks. A block of data is transmitted from DMD to NGD (step 660) using communications link established in step 615. Software codes determine if more data are present or are expected to be present (step 665). Software codes repeat optional data modification 655 and block transmission 660 until all data have been transmitted, at which time an "end of data" marker is transmitted to NGD (step 670). Alternatively, an "end of data" marker may not be needed if, at some point, NGD is informed about the quantity of data to expect and monitors the quantity of data arriving. Steps to check for, and respond to, error conditions are not shown. For example, periodic checks of the communications connection between DMD and NGD are prudent. As an additional example, re-computation of checksums after transmission may disclose an inconsistency and prompt re-transmission of a block of data. FIG. 12 shows details of electronically transmitting data from network gateway device to service center 140 (step 635). The figure is merely an example, which should not unduly limit the scope of the claims herein. Of note, data arriving at NGD in step 625 may arrive over a long period of time. Thus, the steps shown in this figure may await receipt of all data being transmitted, or may proceed after only a portion of data is received. NGD communicates with network of computers 285 at service center 140 via an electronic communication network 150 ("ECN"). Electronic communication between NGD and ECN is established; if necessary, NGD and a connection to ECN are placed in physical proximity to each other (step 710) so that electronic communication between NGD and ECN may occur. The necessary degree of proximity will be determined by the nature of the communications link between NGD and ECN.

A communications connection between NGD and network of computers 285 is established across ECN (step 715). This may be done by a variety of methods known in the art, for example, using protocols such as TCP/IP. Establishing communications connection (step 715) may include protocols such as "handshaking" between NGD and network of computers.

Data are transmitted from NGD to network of computers in a plurality of steps. Before transmitting, data are optionally modified (step 720). For example, a "header" may be attached to data (or a subset of data) by communications protocols such as TCP/IP. As a further example, checksums may be computed for the data (or a subset of the data). As a further example, data archived or buffered on NGD may be permanently removed from storage on NGD as data are prepared to move to network of computers.

In one embodiment, the data (possibly of large size) on NGD are divided into smaller-sized blocks. A block of data is transmitted from NGD to network of computers at service center (step 725) using communications link established in step 715. Software codes determine if more blocks of data are present or are expected to be present (step 730). Software codes repeat optional data modification 720 and transmission of blocks 725 until all data have been transmitted, at which time an "end of data" marker may optionally be transmitted to NGD. Again, steps to check for, and respond to, error conditions are not shown. After completing data transmission, additional actions may be taken on data residing on NGD (step 735), e.g. deleting temporarily-stored data.

Figure 13:
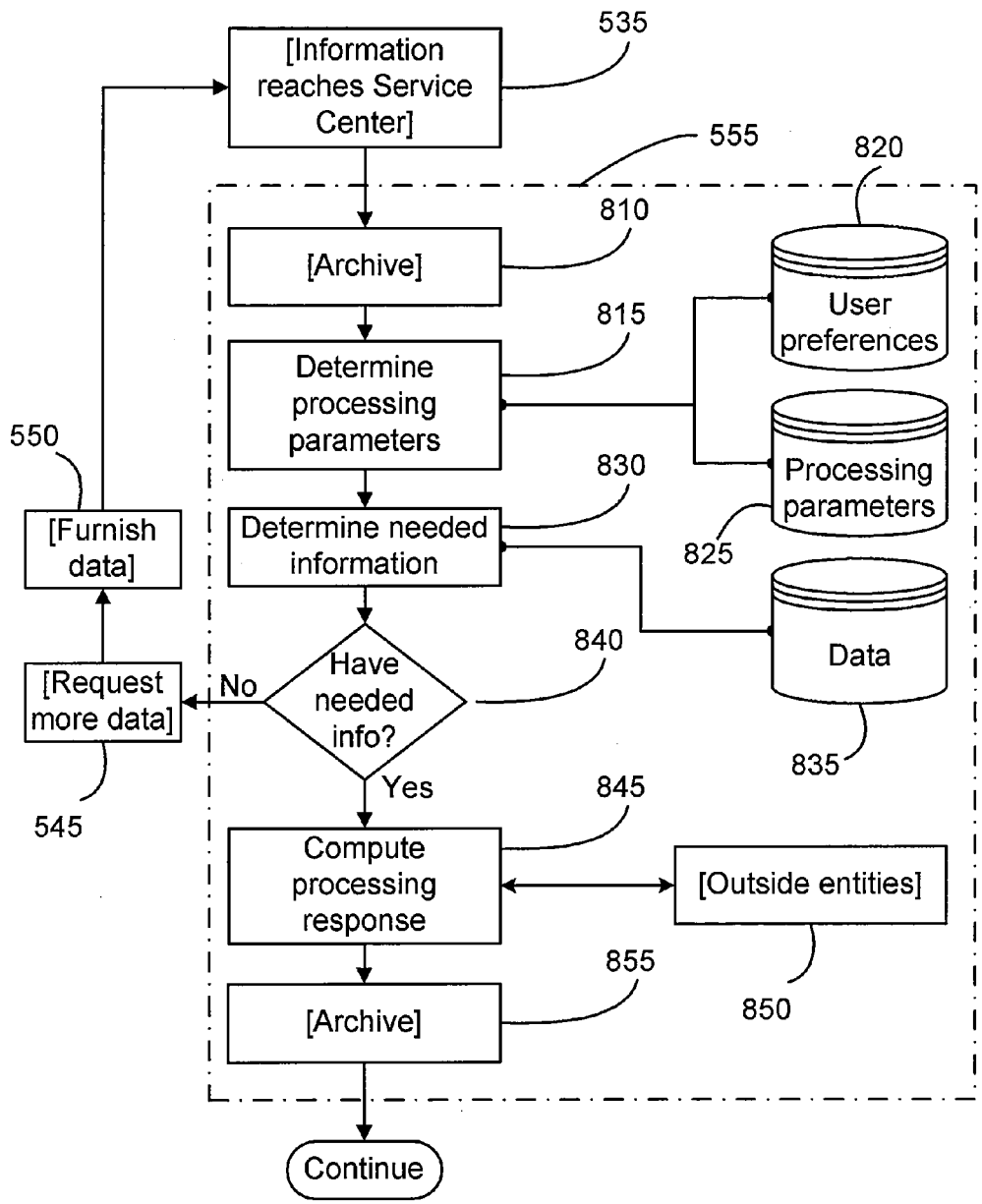
FIG. 13 shows details of processing information related to physiological signals according to an embodiment of the present invention.

FIG. 13 shows details of processing the information related to the physiological signals (step 555) at service center 140. The figure is merely an example, which should not unduly limit the scope of the claims herein. One of ordinary skill in the art would recognize many other variations, modifications, and alternatives. After information arrives at network of computers 285 in service center 140, information is optionally archived (step 810), perhaps in data repository 290, for later retrieval. Before processing can be performed, the parameters of the processing must be determined (step 815), e.g. what specific processing is being requested, what options of the processing are to be employed, etc. As an example, for an adult an apneic episode in sleep is generally defined as lasting 10 seconds or longer; for a child the duration threshold is lower. Thus, the "apnea duration threshold" is an example of a parameter associated with the processing. Processing parameters may be stored in one or more databases, for example, a database of user preferences 820, or a database of parameters 825; such databases may be components of data repository 290. Note that processing parameters may be derived from case data, e.g. age, and that processing of case data may be performed to determine proper parameter(s) to be used in subsequent processing.

Additional data may be needed to perform the processing. Thus, the invention determines whether it has sufficient data needed to perform the processing (step 830), and, if necessary, retrieves additional data from available sources 835 within the service center network of computers. For example, a database of patient medications may be queried to see if the patient is taking agent(s) that might interfere with one or more analyses.

If there is still not sufficient data to perform the processing (this check is performed in step 840), additional data may be requested from a source or sources outside of the service center network of computers (step 545). Data furnished in response to this request (step 550) reaches the service center network of computers by any of a variety of means (step 535). The processing request is then re-considered, as described above.

Once there is sufficient data to compute some or all of the processing response, the response or partial response is computed (step 845). Note that some processing may be architected such that responses may be computed incrementally. That is, responses may be computed on subsets of information. Optionally, the responses to subsets of information would later be unified into a single response (not shown). Also note that third-party data 850 may be needed to perform the processing. The results of the processing are optionally archived in the service center (step 855). The results of the processing may be distributed to some number of end-users, as discussed earlier.

In step 535, information that did not enter DMD 210 in patient home 110 may also be used in processing. Merely by way of example, such information may be loaded onto DMD 210 in step 435, as mentioned earlier. As another example, information may arrive via electronic communications network 150 as the result of a human interaction with a network interface device such as NID 230, NID 255, or other NID. As a further example, data may arrive from an external database. In many cases, data may be conveniently transmitted to service center 140 using electronic communications network 150 using steps 625, 630, and 635.

Figure 14:
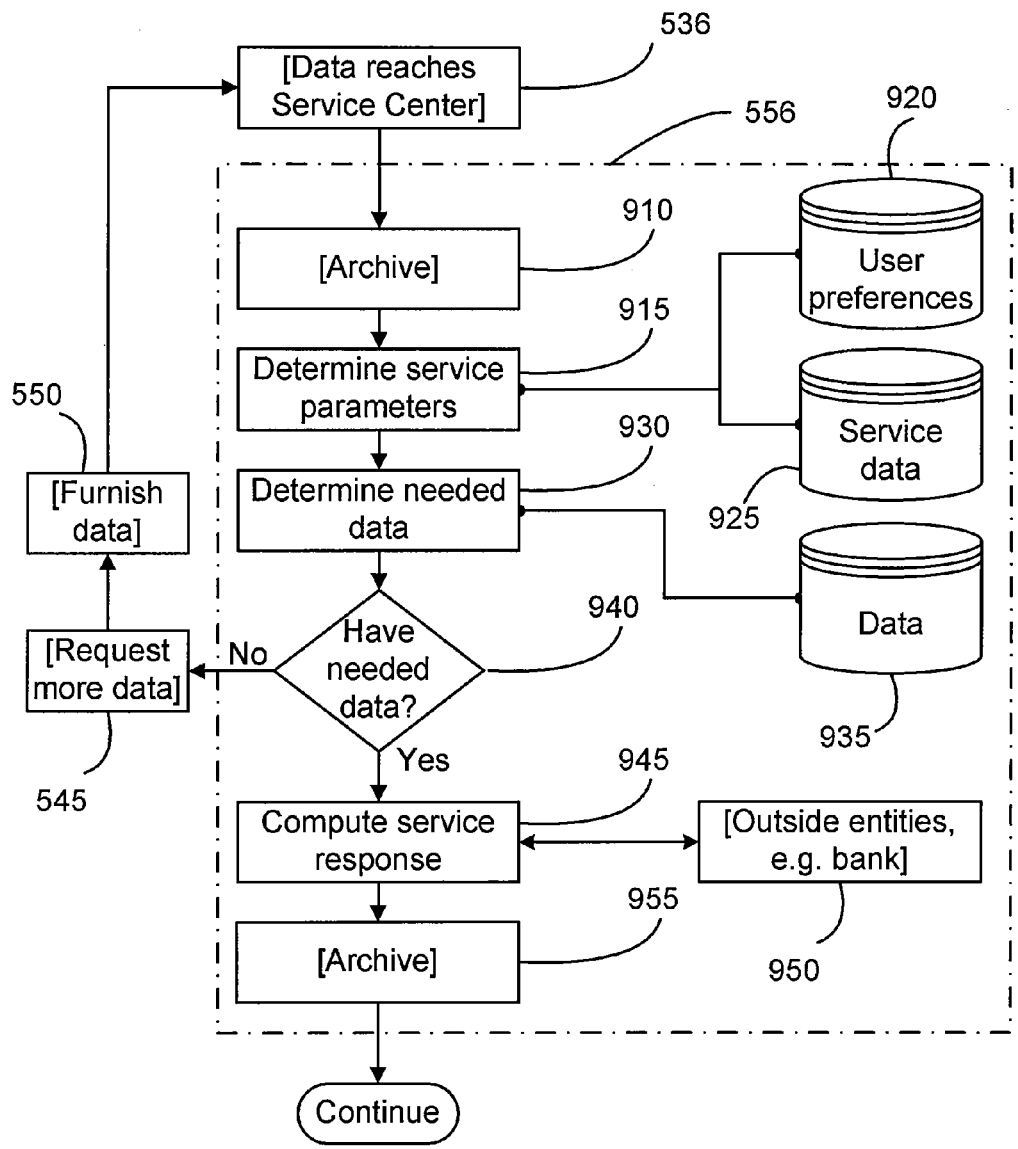
FIG. 14 shows details of performing a service according to an embodiment of the present invention.

As noted earlier, the present invention is capable of performing numerous services for end-users. It is an advantage of the present invention that the design used to process information related to physiological signals can be applied to the performance of other services. This is apparent by comparing FIG. 13 and FIG. 14 and noting their similarities. FIG. 14 shows details of performing a service (step 556). The figure is merely an example, which should not unduly limit the scope of the claims herein. One of ordinary skill in the art would recognize many other variations, modifications, and alternatives.

Services are initiated with a service request (not shown—however, a service request may be an action such as 325A, 325B, or 325C). A service request may optionally be archived (step 910). Before the service can be performed, the parameters of the service must be determined (step 915), e.g. what specific service is being requested, what options of the service are to be employed, etc. As an example, the supply service may have options for automatic disbursement of replacement supplies on a monthly or weekly basis. Service parameters may be stored in one or more databases, for example, a database of user preferences 920, or a database of services 925; such databases may be components of data repository 290. Note that service parameters may be derived other service parameters.

Additional data may be needed to perform the service. For example, the supply service may need to know the current price of specific supply items. Thus, the invention determines whether it has sufficient data needed to perform the service (step 930), and, if necessary, retrieves additional data from available sources 935 within the service center network of computers. In the example above, a database of prices may be queried to retrieve the current prices of specific supply items.

If there is still not sufficient data to perform the service (this check is performed in step 940), additional data may be requested from a source or sources outside of the service center network of computers (step 545). Data furnished in response to this request (step 550) reaches the service center network of computers by any of a variety of means (step 536). The service request is then re-considered, as described above.

Once there is sufficient data to compute some or all of the service response, the response or partial response is computed (step 945). Note that some services may be architected such that responses may be computed incrementally. That is, responses may be computed on subsets of data. Optionally, the responses to subsets of data would later be unified into a single response (not shown). Also note that third-party data 950 may be needed to perform the service, as in a credit card transaction with a bank. The results of the service are optionally archived in the service center (step 955). The results of the service may be distributed to some number of end-users, as discussed earlier.

In step 536, information that did not enter DMD 210 in patient home 110 may also be used in processing. Merely by way of example, such information may be loaded onto DMD 210 in step 435, as mentioned earlier. As another example, information may arrive via electronic communications network 150 as the result of a human interaction with a network interface device such as NID 230, NID 255, or other NID. As a further example, data may arrive from an external database. In many cases, data may be conveniently transmitted to service center 140 using electronic communications network 150 using steps 625, 630, and 635. In some embodiments, steps 536 and 556 may be integrated with processing of control information (steps 540, 585, 560, etc.), akin to the integration of steps 535 and 555, respectively, in FIG. 9.

Additional examples illustrate some of these features of the invention. In one example, mammalian patient 200 may visit a physician's office and complete a symptom questionnaire or other form requesting clinical data. Such data could be stored on DMD 210 in step 435. Such data could be transmitted to service center 140 in step 530 and step 535, thereby making it available in step 556 for processing as data related to the service. Of course, other types of data, such as service data, may be stored on DMD 210 in step 435 and be transmitted later. Several different types of data may simultaneously be in storage on DMD 210.

In another example, data may be furnished (step 550) to service center 140 even when not specifically requested by step 545. For example, mammalian patient 200 may drop off DMD 210 at physician's office after having slept with it the night before. A nurse in the physician's office may ask mammalian patient 200 questions about the hours and subjective quality of sleep the night before, about medication and alcohol use, and so on. The nurse may enter these data into a desktop computer and transmit the data to service center 140 via electronic network 150. These data may then be used in a variety of services and processings.

Note that results may include the results of a plurality of services, not all of which have been explicitly requested, e.g. relevant resources (possibly advertisements) may be returned with the report. Results may also suggest or offer to perform additional services, e.g. prepare documents to assist the physician (or other health care professional) in securing reimbursement from a third-party payor. Such documents might include a HCFA form 1500 or a letter of medical necessity and might incorporate patient-specific clinical and/or administrative data.

Security is often an issue when potentially sensitive medical data are being manipulated. A feature of the invention is that communications across electronic communications network 150 may be performed with a variety of security features. For example, confidential information may be encrypted, which is possible using methods known to persons skilled in the art. However, because encryption has certain disadvantages (e.g. adding overhead to transmission), it may be desirable to minimize encryption without compromising confidential information. One approach to achieve this is to anonymize a portion of the information. Anonymization may be useful in cases where information is not sensitive unless it can be associated with a particular person or other entity. Anonymization blocks the ability of unauthorized parties to make such associations directly. Authorized parties can later reconstruct the association. Merely by way of example, an arbitrary code (e.g. "007-orange-buffalo") may be assigned to a patient by a nurse in a physician's office, and this code may be used to identify the patient to service center 140. Thus, the patient's true identity is never transmitted over electronic communications network 150. As another example, the patient's true identity may be sent, encrypted, to service center 140 which, in turn, assigns an arbitrary unique code to the patient and sends the code back to the end-user site, where it is used to identify the patient. In both cases, authorized parties can make the direct association of data with the patient's actual identity.

An additional feature of the system is the possibility of using DMD 210 as a physical token to enhance security of communications across electronic communications network 150. For example, each DMD 210 may be configured with a unique identification code. In such a case, merely by way of example, the invention may be configured so that communications are not relayed to service center 140 unless accompanied by a valid identification code obtained from a DMD 210 that is simultaneously connected to electronic communications network 150. As a further example, the identification code in DMD 210 may be components of a public-key cryptography system. As still a further example, a code in DMD 210 may change over time according to a certain algorithm.

Yet another feature of the system is the possibility of freeing the end-user from installing client software on their desktop computer or other network interface device beyond commonly bundled software such as a web browser. Merely by way of example, an applet might run in the desktop computer's web-browser via a plug-in such as the Java 1.3 plug-in. The applet could read and write data from DMD 210 and could communicate with service center 140 via electronic communications network 150. The applet would not require end-user to install it on the desktop computer, because it would be downloaded from network of computers 285 at service center 140 as needed. The web-browser might cache the applet on the desktop computer, but this step would be largely invisible to end-user. Furthermore, because many web-browsers contain means to identify when a cached item has been superseded by a new version of the item, it is likely that end-user need not have concerns about executing a manual step in order to have the most recent version of the applet.

Limiting the amount of software installed on desktop computers and other devices at the end-user facility is a security advantage because it reduces the risk of misconfiguration, as different software packages may interfere with each other. It also reduces the need to restrict physical access to equipment, since the software configuration of the equipment is less sensitive to disruption. It may also be possible to develop means to verify aspects of web browser operation, e.g. "test pages", which would add confidence that the desktop computer is properly configured.

The occasional existence of a communications link between DMD 210 and service center 140 adds an additional advantage: the software residing on DMD 210 may be examined from time to time to see if it is the most recent version or if it meets other criteria. Should new software or a modification of software be indicated, such changes may be effected without significant intervention by a human. Software in other devices may be similarly updated. It should be understood that several steps have not been shown above. For example, the process may be interrupted at a plurality of steps; recovery from such interruptions has not been shown. As a further example, authentication measures may be inserted at a plurality of steps in the process, and they have not been shown. As an additional example, a record of all steps and activities may be kept; the contributions to such a record have not been shown. As viewed by the end-user, novel features of the present invention (a) simplify the acquisition of physiologic signals, (b) simplify the transmission of information between various facilities, (c) support administrative functions, (d) simplify the analysis of physiological data, (e) simplify the maintenance of diagnostic equipment, including lessening the need for manual updates of software, (f) simplify data management tasks, (g) incur minimal training costs, (h) generate results promptly at the point of care, and (i) can be implemented to comply with certain provisions of the Health Insurance Portability and Accountability Act.

It should be noted that the above sequence of steps is merely illustrative. The steps can be performed using computer software or hardware or a combination of hardware and software. Any of the above steps can also be separated or be combined, depending upon the embodiment. In some cases, the steps can also be changed in order without limiting the scope of the invention claimed herein. One of ordinary skill in the art would recognize many other variations, modifications, and alternatives. It is also understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method for evaluating sleep disorders in mammals and distributing control information related to the sleep disorders through electronic communication networks, the method comprising:

acquiring analog information related to physiological signals through a mobile device from a mammal user, the mammal user being at a geographic location outside of a sleep laboratory staffed by trained technicians, the mobile device coupled to one or more sensing devices, the sensing device(s) being coupled to one or more monitoring regions of the mammal, the sensing device(s) comprising at least an external microphone device for acquiring the analog information related to the physiological signals;

converting the analog information into a digital format using a signal processing device;

transmitting information related to the physiological signals in the digital format to one or more service computers through an electronic communications network, one or more of the service computers being operably coupled to a health information service facility;

determining if the mammal user has related control information at one of the health information service facilities, the related control information being received through the communication network;

processing the information related to the physiological signals at one or more of the service computers to provide a report associated with the information related to the physiological signals and the mammal user; and communicating report information in the report associated with the information related to the physiological signals directed to evaluating a sleep disorder upon indication of receipt of at least control account information of the mammal user based upon the determining the related account information.

2. The method of claim 1 wherein the geographic location is the home or residence of the mammal user.

3. The method of claim 1 wherein the geographic location is a nursing home or skilled nursing facility.

4. The method of claim 1 wherein the geographic location is a hospital room.

5. The method of claim 1 wherein the processing includes identifying a sleep disorder, the sleep disorder being selected from at least one selected from sleep apnea, the upper airway resistance syndrome, periodic leg movements of sleep, or Cheyne-Stokes respiration.

6. The method of claim 1 wherein the processing includes identifying a sleep disorder, the sleep disorder being snoring.

7. The method of claim 1 wherein the determining is provided before processing.

8. The method of claim 1 wherein the determining is provided after or concurrently with processing.

9. The method of claim 1 wherein the one or more of the monitoring regions includes a neck portion.

10. The method of claim 1 wherein one or more of the monitoring regions includes a suprasternal notch.

11. The method of claim 1 wherein one or more of the monitoring regions is selected from regions of the thorax including the pericardium, the sternal area, the anterior chest, and the esophagus.

12. The method of claim 1 wherein one or more of the monitoring regions is selected from forearm, hand, finger, leg, or toe.

13. The method of claim 1 wherein one or more of the monitoring regions is selected from regions of the head including scalp, face, ear lobe, forehead, supra-orbital area, nares, mouth, philtrum, or submental area.

14. The method of claim 1 wherein one or more of the monitoring regions is selected from an abdomen or penis.

15. A system for evaluating sleep disorders in mammals and distributing control information related to the sleep disorders through electronic communication networks, the system comprising one or more memories, the one or more tangible computer readable memories including:

a code directed to acquiring analog information related to physiological signals through a remote device from a mammal user, the mammal user being at a geographic location outside of a sleep laboratory staffed by trained technicians, the remote device coupled to one or more sensing devices, the sensing device(s) comprising an external microphone device and being coupled to one or more monitoring regions of the mammal;

a code directed to converting the analog information into a digital format using a signal processing device;

a code directed to transmitting information related to the physiological signals in the digital format to one or more service computers through an electronic communications network, each of the service computers being operably coupled to a health information service facility;

a code directed to determining if the mammal user has related control information at one of the health information service facilities, the related control information being received through the communication network;

a code directed to processing the information related to the physiological signals at one or more of the service computers to provide a report associated with the information related to the physiological signals and the mammal user; and a code directed to communicating report information in the report associated with the information related to the physiological signals directed to evaluating sleep disorder upon indication of receipt of at least control account information of the mammal user based upon the determining the related account information.

16. The system of claim 15 wherein the geographic location is the home or residence of the mammal user.

17. The system of claim 15 wherein the geographic location is a nursing home or skilled nursing facility.

18. The system of claim 15 wherein the geographic location is a hospital room.

19. The system of claim 15 wherein the one or more monitoring regions is the neck.

20. The system of claim 15 wherein the one or more monitoring regions is the suprasternal notch.

21. The system of claim 15 wherein the one or more monitoring regions is selected from regions of the thorax including the pericardium, the sternal area, the anterior chest, and the esophagus.

22. The system of claim 15 wherein the one or more monitoring regions is selected from forearm, hand, finger, leg, or toe.

23. The system of claim 15 wherein the one or more monitoring regions is selected from regions of the head including scalp, face, ear lobe, forehead, supra-orbital area, nares, mouth, philtrum, or submental area.

24. The system of claim 15 wherein the one or more monitoring region is selected from abdomen or penis.

25. A controlled method for evaluating sleep disorders in mammals and distributing information including case data related to the sleep disorders through communication networks, the method comprising:

capturing analog information related to physiological signals through a remote device from a mammal user outside of a sleep laboratory staffed by trained technicians, the remote device including a receiving device comprising an external microphone device coupled to the mammal;

converting the analog information into a digital format using a signal processing device;

transmitting information related to the physiological signals in the digital format to one or more service computers through an electronic communications network, each of the service computers being geographically located at a service facility;

transferring case data information related to the physiological signals to the service center receiving the physiological signals;

processing the information related to the physiological signals at one or more of the service facilities to form an output associated with the information and the mammal user;

associating a portion of the case data information to signals associated with the output associated with the physiological signals to form a report; and communicating report information in the report derived from the information related of the physiological signals directed to evaluating a sleep disorder and case data.

26. The method of claim 25 wherein the geographic location is the home or residence of the mammal user.

27. The method of claim 25 wherein the geographic location is a nursing home or skilled nursing facility.

28. The method of claim 25 wherein the geographic location is a hospital room.

29. The method of claim 25 wherein the associating includes processing the information related to the physiological signals with the portion of the case data.

30. The method of claim 25 wherein the processing comprises identifying an age characteristic of the mammal user and using a predetermined process from a plurality of processes based upon the age characteristic.

31. The method of claim 25 wherein the case data are physiological meta data.

32. The method of claim 25 wherein the case data are clinical data.

33. A controlled system for evaluating sleep disorders in mammals and distributing information including case data related to the sleep disorders through communication networks, the system comprising one or more memories, the one or more tangible computer readable memories including:

a code directed to capturing analog information related to physiological signals through a remote device from a mammal user outside of a sleep laboratory staffed by trained technicians, the remote device including a receiving device comprising an external microphone device coupled to the mammal;

a code directed to converting the analog information into a digital format using a signal processing device;

a code directed to transmitting information related to the physiological signals in the digital format to one or more service computers through an electronic communications network, each of the service computers being geographically located at a service facility;

a code directed to transferring case data information related to the physiological signals to the service center receiving the physiological signals;

a code directed to processing the information related to the physiological signals at one or more of the service facilities to form an output associated with the information and the mammal user;

a code directed to associating a portion of the case data information to the output associated with the physiological signals to form a report; and a code directed to communicating report information in the report derived from the information related of the physiological signals directed to evaluating sleep disorder and case data.

34. The system of claim 33 wherein the geographic location is the home or residence of the mammal user.

35. The system of claim 33 wherein the geographic location is a nursing home or skilled nursing facility.

36. The system of claim 33 wherein the geographic location is a hospital room.

37. The system of claim 33 wherein the associating includes processing the information related to the physiological signals with the portion of the case data.

38. The system of claim 33 wherein the processing comprises identifying an age characteristic of the mammal user and using a predetermined process from a plurality of processes based upon the age characteristic.

39. The system of claim 33 wherein the case data are physiological case data.

40. The system of claim 33 wherein the case data are clinical data.

* * * * *